US008889905B2

(12) United States Patent  
Bassler et al.

(10) Patent No.: US 8,889,905 B2
(45) Date of Patent: Nov. 18, 2014

(54) PROCESS FOR PREPARING FORMIC ACID

(71) Applicant: BASF SE, Ludwigshafen (DE)

(72) Inventors: Peter Bassler, Viernheim (DE); Stefan Rittinger, Mannheim (DE); Daniel Schneider, Mannheim (DE); Donata Maria Fries, Mannheim (DE); Klaus-Dieter Mohl, Hockenheim (DE); Joaquim Henrique Teles, Waldsee (DE); Martin Schäfer, Grünstadt (DE); Jürgen Paschold, Hochspeyer (DE)

(73) Assignee: BASF SE, Ludwigshafen (DE)

( * ) Notice: Subject to any disclaimer, the term of this patent is extended or adjusted under 35 U.S.C. 154(b) by 54 days.

(21) Appl. No.: 13/721,392

(22) Filed: Dec. 20, 2012

(65) Prior Publication Data
US 2014/0018456 A1 Jan. 16, 2014

Related U.S. Application Data

(60) Provisional application No. 61/577,701, filed on Dec. 20, 2011.

(51) Int. Cl.
C07C 53/00 (2006.01)
C07C 51/44 (2006.01)

(52) U.S. Cl.
CPC ..................................... C07C 51/44 (2013.01)
USPC ........................................................ 562/609

(58) Field of Classification Search
None
See application file for complete search history.

(56) References Cited

U.S. PATENT DOCUMENTS

| 4,217,460 | A | 8/1980 | Hohenschutz et al. |
| 4,218,568 | A | 8/1980 | Hohenschutz et al. |
| 5,294,740 | A | 3/1994 | Kiefer et al. |
| 2008/0097126 | A1 | 4/2008 | Karl et al. |
| 2010/0063320 | A1 | 3/2010 | Challand et al. |
| 2010/0126843 | A1 | 5/2010 | Stabel et al. |
| 2010/0331573 | A1 | 12/2010 | Schaub |

FOREIGN PATENT DOCUMENTS

| CA | 2774151 A1 | 1/2012 |
| DE | 2545658 A1 | 4/1977 |
| DE | 3428319 A1 | 2/1986 |
| DE | 102009046310 A1 | 5/2010 |
| EP | 0 001 432 A1 | 4/1979 |

(Continued)

OTHER PUBLICATIONS

U.S. Appl. No. 13/172,123, filed Jun. 29, 2011, Schaub et al.

(Continued)

*Primary Examiner* — Rosalynd Keys
*Assistant Examiner* — Jennifer C Sawyer
(74) *Attorney, Agent, or Firm* — Drinker Biddle & Reath LLP

(57) ABSTRACT

Process for obtaining formic acid by thermal separation of a stream comprising formic acid and a tertiary amine (I), in which a liquid stream comprising formic acid and tertiary amine (I) is produced by combining tertiary amine (I) and a formic acid source, secondary components comprised therein are separated off, formic acid is removed by distillation from the resulting liquid stream in a distillation apparatus, where the bottom output from the distillation apparatus is separated into two liquid phases, and the upper liquid phase is recirculated to the formic acid source and the lower liquid phase is recirculated to the separation of the secondary components and/or to the distillation apparatus, wherein low boilers are removed by distillation from the upper liquid phase and recirculated to the depleted stream.

11 Claims, 16 Drawing Sheets

(56) References Cited

FOREIGN PATENT DOCUMENTS

| | | |
|---|---|---|
| EP | 0126524 A1 | 11/1984 |
| EP | 0181078 A1 | 5/1986 |
| EP | 0563831 A2 | 10/1993 |
| WO | WO-2006/021411 A1 | 3/2006 |
| WO | WO-2008/116799 A1 | 10/2008 |
| WO | PCT/EP2011/060012 | 1/2012 |
| WO | PCT/EP2011/060770 | 1/2012 |
| WO | WO-2012000799 A1 | 1/2012 |
| WO | WO-2012000964 A1 | 1/2012 |

OTHER PUBLICATIONS

U.S. Appl. No. 13/171,928, filed Jun. 29, 2011, Schaub et al.
U.S. Appl. No. 61/316,841.
U.S. Appl. No. 13/171,598, filed Jun. 29, 2011, Schneider et al.
U.S. Appl. No. 61/392,062.
U.S. Appl. No. 13/330,974, filed Dec. 20, 2011, Schaub et al.
U.S. Appl. No. 13/542,791.
U.S. Appl. No. 61/577,703.
U.S. Appl. No. 13/646,161.
U.S. Appl. No. 61/557,931.
International Search Report for PCT/EP2012/073930, mailing date Feb. 18, 2013.

Example 1

Methyldi-n-hexylamine concentration in stream (8)

Example 2

Methyldi-n-hexylamine concentration in stream (8)

PROCESS FOR PREPARING FORMIC ACID

RELATED APPLICATIONS

This application claims benefit (under 35 USC 119(e)) of U.S. Provisional Application Ser. No. 61/577,701, filed Dec. 20, 2011, which is incorporated herein by reference in its entirety.

BACKGROUND OF THE INVENTION

The present invention relates to a process for obtaining formic acid by thermal separation of a stream comprising formic acid and a tertiary amine (I), in which a liquid stream comprising formic acid and tertiary amine (I) in a molar ratio of from 0.5 to 5 is produced by combining tertiary amine (I) and a formic acid source, and formic acid is removed by distillation at a temperature at the bottom of from 100 to 300° C. and a pressure of from 30 to 3000 hPa abs from the resulting liquid stream in a distillation apparatus, where the bottom output from the distillation apparatus is separated into two liquid phases and the upper liquid phase is recirculated to the formic acid source and the lower liquid phase is recirculated to the removal of the secondary components and/or to the distillation apparatus.

Formic acid is an important and versatile product. It is used, for example, for acidification in the production of animal feeds, as preservative, as disinfectant, as assistant in the textile and leather industry, as a mixture with its salts for deicing aircraft and runways and also as synthetic building block in the chemical industry.

The most widespread process at present for preparing formic acid is the hydrolysis of methyl formate which can be obtained, for example, from methanol and carbon monoxide. The aqueous formic acid obtained by hydrolysis is subsequently concentrated, for example using an extraction auxiliary such as a dialkylformamide (DE 25 45 658 A1).

In addition, obtaining formic acid by thermal dissociation of compounds of formic acid and a tertiary nitrogen base is also known. These compounds are generally acidic ammonium formates of tertiary nitrogen bases, in which the formic acid has reacted beyond the stage of classical salt formation with the tertiary nitrogen bases to form stable addition compounds bridged by hydrogen bonds. The addition compounds of formic acid and tertiary nitrogen bases can be formed by combining the tertiary nitrogen base and a formic acid source. Thus, for example, WO 2006/021,411 discloses the preparation of such addition compounds in general by (i) direct reaction of the tertiary nitrogen base with formic acid, (ii) by transition metal-catalyzed hydrogenation of carbon dioxide to formic acid in the presence of the tertiary nitrogen base, (iii) by reaction of methyl formate with water and subsequent extraction of the resulting formic acid by means of the tertiary nitrogen base and (iv) by reaction of methyl formate with water in the presence of the tertiary nitrogen base.

The general advantages of using addition compounds of formic acid and tertiary nitrogen bases for obtaining formic acid are that the addition compounds firstly bind the formic acid strongly enough to withdraw the formic acid as free formic acid from the medium, for example the reaction medium, in which the formic acid has been formed by chemical synthesis or, for example, from a dilute formic acid solution and thereby allow the formic acid to be separated off more readily in the form of its addition compounds, but are weak enough for the formic acid subsequently to be able to be released again from the addition compounds by thermal dissociation in order to obtain it in concentrated and purified free form.

EP 0 001 432 A discloses a process for obtaining formic acid by hydrolysis of methyl formate in the presence of a tertiary amine, in particular an alkylimidazole, to form addition compounds of formic acid and the tertiary amine. The hydrolysis mixture obtained, which comprises unreacted methyl formate, water, methanol, addition compounds and tertiary amine, is freed of the low boilers methyl formate and methanol in a first distillation column. In a second column, the remaining bottom product is dewatered. The dewatered bottom product from the second column, which still comprises addition compounds and tertiary amine, is then fed to a third column and in this the addition compounds are thermally dissociated into formic acid and tertiary amine. The formic acid liberated is removed as overhead product. The tertiary amine collects in the liquid phase and is recirculated to the hydrolysis.

DE 34 28 319 A discloses a process for obtaining formic acid by hydrolysis of methyl formate. The hydrolysis mixture obtained, which comprises unreacted methyl formate, water, methanol and formic acid, is freed of the low boilers methyl formate and methanol in a first distillation column. The aqueous formic acid obtained at the bottom is subsequently extracted with a relatively high-boiling amine, in particular a relatively long-chain, hydrophobic $C_6$-$C_{14}$-trialkylamine, in the presence of an additional hydrophobic solvent, in particular an aliphatic, cycloaliphatic or aromatic hydrocarbon, and thereby converted into an aqueous addition compound of formic acid and the amine. This is dewatered in a second distillation column. The dewatered addition compound obtained at the bottom is then, according to the teaching of DE 34 28 319 A, fed to the uppermost plate of a distillation column (in FIG. 1 denoted as "K4") and thermally dissociated. The hydrophobic solvent is present both in the overhead stream and the bottoms from the column. The gaseous overhead stream comprises mainly the formic acid liberated together with the hydrophobic solvent. This stream is liquefied again in the condenser. This results in formation of two phases, namely a polar formic acid phase and a hydrophobic solvent phase. The formic acid phase is discharged as product and the solvent phase is returned as runback to the column. Due to the presence of the hydrophobic solvent, complete dissociation of the adduct, which according to the teaching of the DE first publication occurs without decomposition of formic acid, can be achieved. The (virtually) formic acid-free bottoms comprise the hydrophobic amine and the hydrophobic solvent. This is recirculated to the extraction stage.

EP 0 181 078 A and EP 0 126 524 A describe processes for obtaining formic acid by hydrogenation of carbon dioxide in the presence of a transition metal catalyst and a tertiary amine such as a $C_1$-$C_{10}$-trialkylamine to form an addition compound of formic acid and the tertiary amine, work-up of the hydrogenation output to separate off the catalyst and the low boilers, replacement of the amine base by a weaker, higher-boiling tertiary amine, in particular by an alkylimidazole, with splitting-off of the first tertiary amine and subsequent thermal dissociation of the newly formed addition compound in a distillation column. According to EP 0 181 078 A, FIG. 1, the stream comprising formic acid and amine is for this purpose fed into the middle region of the column "30". The formic acid liberated in the thermal dissociation is removed as overhead product. The weaker, higher-boiling tertiary amine collects at the bottom and is recirculated to the stage of base exchange.

WO 2008/116,799 discloses a process for obtaining formic acid by hydrogenation of carbon dioxide in the presence of a transition metal catalyst, a high-boiling polar solvent such as an alcohol, ether, sulfolane, dimethyl sulfoxide or amide and a polar amine bearing at least one hydroxyl group to form an addition compound of formic acid and the amine. According to the teaching of WO 2008/116,799, the hydrogenation output can be fed directly to a distillation apparatus for thermal dissociation of the addition compound. This can comprise a distillation column and, if short residence times are desired, also a thin film evaporator or falling film evaporator. The formic acid liberated is removed as overhead product. The polar amine and the polar solvent and any catalyst which has not been separated off collect at the bottom and can be recirculated to the hydrogenation stage.

WO 2006/021,411 describes a process for obtaining formic acid by thermal dissociation of an addition compound of formic acid and a tertiary amine (quaternary ammonium formate), in which the tertiary amine has a boiling point of from 105 to 175° C. Alkylpyridines are mentioned as preferred tertiary amines. The specific boiling range of the tertiary amines increases the color stability of the formic acid obtained. The addition compound to be used can in general be obtained from the tertiary amine and a formic acid source. The output from the adduct synthesis is advantageously firstly freed of volatile constituents and then fed to the thermal dissociation. The thermal dissociation is carried out as usual in a distillation column, with the stream comprising formic acid and amine being fed as per FIG. 1 of WO 2006/021,411 into the middle region of the column (C). The formic acid liberated is removed as overhead product. The tertiary amine which may still comprise residues of formic acid collects in the liquid phase and can be recirculated to the formic acid source.

EP 0 563 831 A reports an improved process for the thermal dissociation of an addition compound of formic acid and a tertiary amine (quaternary ammonium formate) to give formic acid. The addition compound to be used can in general be obtained from the tertiary amine and a formic acid source. The output from the synthesis is advantageously firstly freed of volatile constituents and then fed into the middle of a distillation column for thermal dissociation. The improvement comprises essentially carrying out the thermal dissociation of the addition compound in the presence of a secondary formamide which increases the color stability of the formic acid obtained. The formic acid liberated is removed as overhead product. The tertiary amine and the secondary formamide collect in the liquid phase and can be recirculated to the formic acid source.

PCT/EP2011/060770 teaches a process for obtaining formic acid by thermal separation of a stream comprising formic acid and a tertiary amine (I), in which combining tertiary amine (I) and a formic acid source produces a liquid stream comprising formic acid and a tertiary amine (I) in a molar ratio of from 0.5 to 5, from 10 to 100% by weight of the secondary components comprised therein are separated off and formic acid is removed by distillation from the resulting liquid stream in a distillation apparatus at a temperature at the bottom of from 100 to 300° C. and a pressure of from 30 to 3000 hPa, and the bottom output from the distillation apparatus is separated into two liquid phases of which the upper liquid phase is enriched in tertiary amine (I) and is recirculated to the formic acid source and the lower liquid phase is enriched in formic acid and is recirculated to removal of the secondary components and/or to the distillation apparatus.

It is an object of the present invention to discover an improved process for obtaining formic acid by thermal separation of a stream comprising formic acid and a tertiary amine, which process has advantages over the prior art and is able to give formic acid in high yield and high concentration. In particular, the improved process should also function stably over long operating times and produce formic acid in constant high purity. The process should naturally be able to be carried out very simply and with a very low energy consumption.

We have surprisingly found a process for obtaining formic acid by thermal separation of a stream comprising formic acid and a tertiary amine (I) which at a pressure of 1013 hPa abs has a boiling point which is at least 5° C. higher than that of formic acid, in which (a) a liquid stream comprising formic acid and tertiary amine (I) and having a molar ratio of formic acid to tertiary amine (I) of from 0.5 to 5 is produced by combining tertiary amine (I) and a formic acid source;

(b) from 10 to 100% by weight of the secondary components comprised therein are separated off from the liquid stream obtained from step (a);

(c) formic acid is removed by distillation from the liquid stream comprising formic acid and tertiary amine (I) obtained from step (b) in a distillation apparatus at a temperature at the bottom of from 100 to 300° C. and a pressure of from 30 to 3000 hPa abs, where the tertiary amine (I) to be used in step (a) and the degree of separation in the abovementioned distillation apparatus are selected so that two liquid phases are formed in the bottom output;

(d) the bottom output from the distillation apparatus mentioned in step (c) is separated into two liquid phases, where the upper liquid phase has a molar ratio of formic acid to tertiary amine (I) of from 0 to 0.5 and the lower liquid phase has a molar ratio of formic acid to tertiary amine (I) of from 0.5 to 4;

(e) the upper liquid phase from the phase separation in step (d) is recirculated to step (a); and (f) the lower liquid phase from the phase separation in step (d) is recirculated to step (b) and/or (c), wherein (g) low boilers which at a pressure of 1013 hPa abs have a boiling point which is at least 5° C. lower than that of the tertiary amine (I) are separated off by distillation from the upper liquid phase from the phase separation in step (d) in a distillation apparatus at a temperature at the bottom of from 100 to 300° C. and a pressure of from 1 to 1000 hPa abs and the stream depleted in low boilers is recirculated to one of the abovementioned steps (a) to (f).

A BRIEF DESCRIPTION OF THE FIGURES

A DETAILED DESCRIPTION OF THE INVENTION

Figure 1:
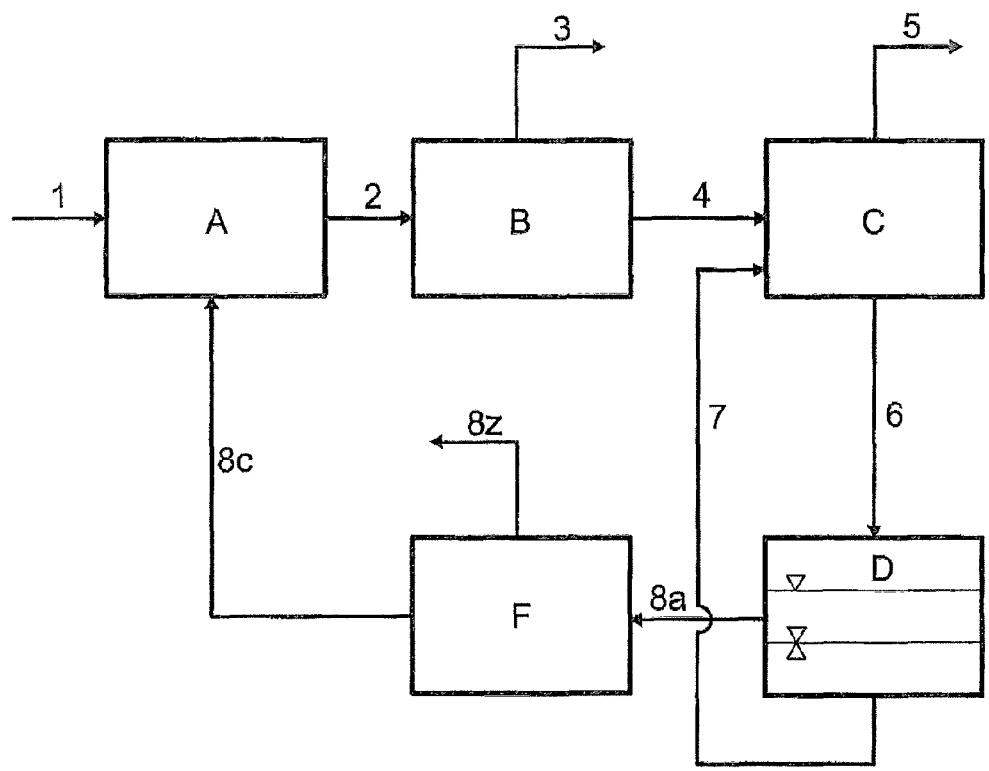
FIG. 1 shows a simplified block diagram of a general embodiment of the process of the invention.

The tertiary amine (I) used in step (a) of the process of the invention has, at a pressure of 1013 hPa abs, a boiling point which is at least 5° C. higher than that of formic acid. The tertiary amine (I) to be used preferably has a boiling point which is at least 10° C. higher, particularly preferably at least 50° C. higher and very particularly preferably at least 100° C. higher, than that of formic acid. A restriction in respect of an upper limit value for the boiling point is not necessary since a very low vapor pressure of the tertiary amine (I) is basically advantageous for the process of the invention. In general, the boiling point of the tertiary amine (I) is below 500° C. at a pressure optionally extrapolated by known methods from vacuum to 1013 hPa abs.

The formic acid source mentioned in step (a) is a stream which comprises formic acid in dilute, contaminated and/or chemically bound form or comprises a precursor from which formic acid is produced by chemical reaction. The formic acid source in step (a) ultimately ensures the direct or indirect introduction of formic acid. Addition in chemically bound form can, for example, be effected in the form of a complex, a salt or an addition compound of formic acid and an amine other than the tertiary amine (I). Possible chemical reactions are in principle all chemical reactions in which formic acid is produced. However, the production of formic acid by hydrolysis of methyl formate and production of formic acid by transition metal-catalyzed hydrogenation of carbon dioxide are of particular industrial importance at the time of the present patent application. Both the possible syntheses mentioned are well known in the art and have been described in a variety of variants and embodiments. A further industrially relevant possibility for producing formic acid by chemical reaction is, for example, direct reaction of carbon monoxide with water.

In the case of the hydrolysis of methyl formate, it is usual to introduce methyl formate, water and tertiary amine (I) either together or in succession into the hydrolysis reactor in order to trap the formic acid formed by hydrolysis in the form of an addition compound by means of the tertiary amine (I) and thus withdraw it from the hydrolysis equilibrium. This makes it possible to achieve a higher conversion of methyl formate and allows particularly advantageous removal of the unreacted water by means of a subsequent distillation.

In the case of the transition metal-catalyzed hydrogenation of carbon dioxide, the tertiary amine (I) is generally introduced into the hydrogenation reactor in order to form a stream comprising formic acid and a tertiary amine (I) in the hydrogenation itself.

The stream comprising formic acid and tertiary amine (I) is preferably produced by hydrolysis of methyl formate in the presence of water and tertiary amine (I) in step (a). Production of the stream comprising formic acid and tertiary amine (I) by concentration of dilute formic acid in the presence of tertiary amine (I) in step (a) is also preferred. However, the stream comprising formic acid and tertiary amine (I) is particularly preferably produced by hydrolysis of methyl formate in the presence of water and tertiary amine (I) in step (a).

The tertiary amine (I) and the formic acid source can be combined in the presence of water in step (a). In the preferred hydrolysis of methyl formate, water is actually needed as reactant for the conversion of methyl formate. If the tertiary amine (I) and the formic acid source are combined in the presence of water in step (a), the content of water is generally set, taking account of the amount of chemically consumed water, so that the liquid stream produced in step (a) comprises not only formic acid and tertiary amine (I) but also water.

The combining of tertiary amine (I) and the formic acid source can be carried out in a variety of ways. If the formic acid source is a stream comprising formic acid in dilute, contaminated and/or chemically bound form, simple contacting, preferably with mixing, with the tertiary amine (I) is often sufficient. This can, for example, be carried out in tubes which preferably comprise suitable mixing internals. Contacting can likewise be carried out in other apparatuses, for example stirred vessels. Stepwise combining in which the tertiary amine (I) is added stepwise to the formic acid source or, conversely, the formic acid source is added stepwise to the tertiary amine (I) is also possible and may even be advantageous. If the formic acid source is a stream from which the formic acid is to be produced from a number of materials by chemical reaction, it is generally advantageous to produce the formic acid source by combining the individual components in the reactor. Possible reactors are, in particular, the reactors known to those skilled in the art for this type of reaction. The tertiary amine (I) can, for example, be initially charged, introduced in parallel to the individual components of the formic acid source, introduced during the course of the chemical reaction or introduced only at the end of the chemical reaction. It is also possible to distribute these individual steps over a plurality of reactors. Depending on the heat involved on combining tertiary amine (I) and the formic acid source, it may be advantageous to cool the apparatus itself or the stream obtained therefrom.

Suitable ways of combining tertiary amine (I) and the formic acid source can be determined without great difficulty on the basis of routine knowledge in the art.

The liquid stream produced on combining tertiary amine (I) and a formic acid source in step (a) has a molar ratio of formic acid to tertiary amine (I) of from 0.5 to 5. The molar ratio is preferably ≥1 and preferably ≤3. The molar ratio mentioned is based on the total liquid stream, regardless of whether it is present as a single phase or a plurality of phases.

The liquid stream comprising formic acid and tertiary amine (I) which is produced in step (a) generally has a concentration of formic acid plus tertiary amine (I) of from 1 to 99% by weight, based on the total amount of the stream. The stream mentioned preferably has a concentration of formic acid plus tertiary amine (I) of ≥5% by weight and particularly preferably ≥15% by weight and also preferably ≤95% by weight and particularly preferably ≤90% by weight.

From 10 to 100% by weight of the secondary components present in the liquid stream obtained from step (a) are separated off from this liquid stream. The range mentioned is based on the concentration of secondary components in the liquid stream produced in step (a). This concentration will hereinafter be referred to as "$C_{secondarycomponents}$ (stream from step (a))". The liquid stream depleted in secondary components corresponds to the stream which is fed to the distillation apparatus as per step (c). This concentration will hereinafter be referred to as "$C_{secondarycomponents}$ (feed stream to step (c))". The abovementioned removal of secondary components is thus based on the quotient $$1 - \frac{C_{secondarycomponents} \text{ (feed stream to step } (c)\text{)[g/l]}}{C_{secondarycomponents} \text{ (stream from step } (a)\text{)[g/l]}} \cdot 100\% \text{ by weight}$$

Preference is given to ≥20% by weight and particularly preferably ≥30% by weight and also preferably ≤99.99% by weight and particularly preferably ≤99.9% by weight of the secondary components being separated off in step (b).

Here, the term secondary components refers to all components which are comprised in the liquid stream obtained in step (a) and are neither formic acid nor tertiary amine (I). Examples which may be mentioned are water, methanol (in particular in the case of the hydrolysis of methyl formate), dissolved unhydrolyzed methyl formate (in particular in the case of the hydrolysis of methyl formate), possible degradation products of the tertiary amine (I), dissolved inert gases, homogeneous catalyst (in particular in the case of the hydrogenation of carbon dioxide), dissolved carbon dioxide or dissolved hydrogen (in particular in the case of the hydrogenation of carbon dioxide), solvents, other components.

The way in which the secondary components may be separated off is inconsequential for the process of the invention. Thus, for example, it is possible to use the customary and known methods for the separation of liquid mixtures. Particular mention may be made of separation by distillation. In this case, the liquid mixture is separated in a distillation apparatus. Thus, for example, low-boiling secondary components such as methanol, methyl formate or water can be separated off at the top or as a side offtake stream. However, it is also conceivable to separate off high-boiling secondary components at the bottom and the mixture comprising formic acid and tertiary amine (I) as side stream or overhead product. Apart from separation by distillation, membrane, absorption, adsorption, crystallization, filtration, sedimentation or extraction processes are, however, also possible. Preference is given to extraction processes in the concentration of dilute aqueous formic acid and the use of tertiary amines (I) which are immiscible or only miscible to a small extent with water.

It is naturally also possible to combine a plurality of separation steps which may also be based on different methods. The design of the separation step or separation steps can be undertaken using conventional technical knowledge.

Of course, further process steps apart from step (b) can be carried out between steps (a) and (c) in the process of the invention.

Finally, formic acid is removed by distillation in a distillation apparatus at a temperature at the bottom of from 100 to 300° C. and a pressure of from 30 to 3000 hPa abs from the liquid stream obtained from step (b). As distillation apparatuses for this purpose, it is in principle possible to use the apparatuses known to those skilled in the art for such separation tasks or can be designed by a person skilled in the art using general technical knowledge.

The distillation apparatus usually comprises not only the actual column body with internals but also, inter alia, an overhead condenser and a bottom vaporizer. In addition, these can naturally also comprise further peripheral apparatuses or internals, for example a flash vessel in the feed line (for example to separate gas and liquid in the feed to the column body), an intermediate vaporizer (for example for improved heat integration of the process) or internals for avoiding or reducing aerosol formation (for example heatable trays, demisters, coalescers or deep-bed diffusion filters). The column body can be equipped, for example, with ordered packing, random packing elements or trays. The number of theoretical plates required is dependent, in particular, on the type of tertiary amine (I), the concentration of formic acid and tertiary amine (I) in the feed to the distillation apparatus in step (c) and the desired concentration or the desired purity of the formic acid, and can be determined in a conventional way by a person skilled in the art. The number of theoretical plates required is generally ≥3, preferably ≥6 and particularly preferably ≥7. There are in principle no upper limits. However, for practical reasons it will be usual to use generally ≤70, optionally ≤50, theoretical plates or even ≤30 theoretical plates.

The stream comprising formic acid and tertiary amine (I) from step (b) can be fed, for example, as side stream to the column body in the distillation apparatus.

A flash evaporator, for example, can optionally also precede the addition. To keep the thermal stress on the stream fed into the distillation apparatus as small as possible, it is generally advantageous to feed this in in a relatively low region of the distillation apparatus. Thus, in step (c), the stream comprising formic acid and tertiary amine (I) is preferably fed in in the region of the lower quarter, preferably in the region of the lower fifth and particularly preferably in the region of the lower sixth, of the theoretical plates present, with direct introduction into the bottom naturally also being comprised here.

As an alternative, preference is also given, in step (c), to feed said stream comprising formic acid and a tertiary amine (I) from step (b) into the bottom vaporizer of the distillation apparatus.

The distillation apparatus is operated at a temperature at the bottom of from 100 to 300° C. and a pressure of from 30 to 3000 hPa abs. The distillation apparatus is preferably operated at a temperature at the bottom of ≥120° C., particularly preferably ≥140° C., and preferably ≤220° C. and particularly preferably ≤200° C. The pressure is preferably ≥30 hPa abs, particularly preferably ≥60 hPa abs, and preferably ≤1500 hPa abs and particularly preferably ≤500 hPa abs.

Depending on the composition and origin of the feed comprising formic acid and a tertiary amine (I) to the distillation apparatus, formic acid can be obtained as overhead product and/or side product from the distillation apparatus. If the feed comprises constituents having boiling points lower than that of formic acid, it may be advantageous to separate these off as overhead product and separate off the formic acid at a side offtake in the distillation. In the case of possible dissolved gases (for example carbon monoxide or carbon dioxide) in the feed, it is generally also possible to separate off the formic acid together with these as overhead product. If the feed comprises constituents having boiling points higher than that of formic acid, formic acid is preferably separated off by distillation as overhead product, but optionally instead or additionally in the form of a second stream at the side offtake. The constituents which have boiling points higher than that of formic acid are in this case preferably taken off in an additional side stream. The side stream comprising secondary components can optionally be recirculated to step (b) in order to separate off the secondary components.

Formic acid having a content of up to 100% by weight can be obtained in this way. In general, formic acid contents of from 75 to 99.995% by weight can be achieved without problems. The balance to 100% by weight is mainly water, with other components such as solvents or possible decomposition products naturally also being conceivable as materials apart from formic acid and the tertiary amine (I) introduced into the distillation apparatus. Thus, water can, for example, be comprised in the feed to the distillation apparatus or else may also be formed in small amounts only in the thermal separation by decomposition of formic acid.

In the isolation of concentrated formic acid having a content of from 95 to 100% by weight as overhead or side product, water is discharged in a side stream together with part of the formic acid split off. The formic acid content of the side stream is typically from 75 to 95% by weight. The aqueous formic acid in the side stream can optionally be recirculated to step (b) in order to separate off the water.

However, it is also possible to discharge the water and the formic acid split off in a joint overhead or side stream. The formic acid content of the product obtained in this way is then generally from 85 to 95% by weight.

To largely suppress, in particular, the formation of organic decomposition products of the tertiary amine (I) which are formed by oxidation, it is particularly advantageous, especially when the distillation apparatus is operated at pressures below 0.1 MPa abs, for the intrusion of oxygen through a large number of connections, ports and flanges to be avoided or at least kept extremely low by special care during installation, by use of particularly well-sealed flange connections (for instance those having comb profile seals or weld lip seals) or by means of nitrogen-blanketed flange connections. A suitable flange connection is disclosed, for example, in DE 10 2009 046 310 A1.

The formic acid which can be obtained by the process of the invention has a low color number and also a high color number stability. In general, a color number of ≤20 APHA, in particular even ≤10 APHA and possibly even ≤5 APHA, can be achieved without problems. Even on storage for a number of weeks, the color number remains virtually constant or increases only insignificantly.

Owing to the removal of the organic decomposition products of the tertiary amine (I) according to the invention in step (b), a particularly pure formic acid in which said decomposition products are generally present in a concentration of ≤70 ppm by weight, preferably ≤30 ppm by weight and very particularly preferably ≤20 ppm by weight, can be obtained without a further outlay.

The content of secondary components is extremely low and is generally ≤100 ppm by weight, preferably ≤50 ppm by weight and very particularly preferably ≤25 ppm by weight.

It may also be advantageous to use a plurality of distillation apparatuses in step (c), particularly when further fractions, for example accompanying materials comprised, reaction by-products, impurities and/or formic acid fractions of various purities and concentrations, are to be obtained in addition to the free formic acid and the amine (I)-comprising bottom product.

The distillation apparatus for separating off the formic acid can naturally also be configured as thermally coupled distillation columns or as a dividing wall column.

In the process of the invention, the tertiary amine (I) to be used in step (a) and the degree of separation in the distillation apparatus mentioned in step (c) are selected so that two liquid phases are formed in the bottom output from the distillation apparatus mentioned in step (c).

The formation of two liquid phases is determined mainly by the chemical and physical properties of the two phases. These can in turn be influenced by the choice of the tertiary amine (I) to be used, by the degree of separation in the distillation apparatus and also by the presence of any additional components such as solvents and the concentrations thereof.

For the present purposes, the degree of separation is the quotient $$\frac{m_{formic\ acid}(\text{feed stream to step }(c))[g/h] - m_{formic\ acid}(\text{bottom output})[g/h]}{m_{formic\ acid}(\text{feed stream to step }(c))[g/h]} \cdot 100\%$$

where "$m_{formic\ acid}$(feed stream to step (c))" is the amount of formic acid fed per unit time to the distillation apparatus and "$m_{formic\ acid}$(bottom output)" corresponds to the amount of formic acid discharged per unit time in the bottom output. In this preferred embodiment of the process of the invention, the degree of separation selected is generally ≥10%, preferably ≥25% and particularly preferably ≥40%, and generally ≤99.9%, preferably ≤99.5% and particularly preferably ≤99.0%. The degree of separation can, for example, be easily influenced by the temperature and pressure conditions in the distillation apparatus and by the residence time in the distillation apparatus. It can be determined by means of simple tests, optionally also during operation of the process of the invention.

The suitability of a tertiary amine (I) or a solvent which is optionally additionally desired can be determined, for example, in simple tests in which the number of phases is determined under the conditions envisaged.

The phase separation can, for example, be carried out in a separate phase separator located downstream of the distillation apparatus. However, it is also possible to integrate the phase separator into the bottom region of the distillation apparatus, in the region of the bottom vaporizer or else in the region of the bottom vaporizer circuit. Here, it is also possible or may even be advantageous to use, for example, a centrifugal separator.

Since the formation of two liquid phases is also influenced by the temperature in addition to the chemical and physical properties of the two phases and the miscibility generally increases with temperature, it may be advantageous to operate the phase separation at a lower temperature than the temperature at the bottom previously selected in order to improve the phase separation. For this purpose, the bottom output is usually cooled to a temperature in the range from 30 to 180° C. in an intermediate heat exchanger. The phase separation is preferably carried out at a temperature of ≥50° C. and at a temperature of ≤160° C. and particularly preferably at a temperature of ≤130° C.

The upper liquid phase in step (d) has a molar ratio of formic acid to tertiary amine (I) of in general from 0 to 0.5, preferably ≥0.005 and particularly preferably ≥0.015 and also preferably ≤0.25 and particularly preferably ≤0.125. The lower liquid phase in step (d) has a molar ratio of formic acid to tertiary amine (I) of in general from 0.5 to 4, preferably ≥0.75 and particularly preferably ≥1 and also preferably ≤3.5 and particularly preferably ≤3. However, depending on the choice of the amine, it can of course also be possible for the phase comprising formic acid to form the upper phase and the amine phase having a molar formic acid/amine ratio of from 0 to 0.5 to form the lower phase. It is merely important that there is a phase separation with one phase having a molar ratio of formic acid to tertiary amine of in general from 0 to 0.5 and a second phase having a molar ratio of formic acid to tertiary amine of in general from 0.5 to 4. The upper phase is preferably that having a molar ratio of formic acid to tertiary amine of in general from 0 to 0.5 and the lower phase is preferably that having a molar ratio of formic acid to tertiary amine of in general from 0.5 to 4.

Furthermore, it is advantageous in the process of the invention to select the degree of separation of the distillation apparatus mentioned in step (c) in such a way that the molar ratio of formic acid to tertiary amine (I) in the bottom output is from 0.1 to 2.0. For the purposes of the present invention, the bottom output is the totality of the liquid bottom condensates which leave the distillation apparatus and are separated into two liquid phases in step (d). It is inconsequential whether the bottom condensates originate, for example, directly from the bottom of the distillation apparatus, the bottom of the bottom vaporizer or from both. The degree of separation of the distillation apparatus mentioned in step (c) is preferably selected so that the molar ratio of formic acid to tertiary amine (I) in the bottom output is preferably ≤1.5.

As a result of the recirculation of the upper liquid phase from the phase separation in step (d) to step (a) as per step (e), the tertiary amine (I) comprised in the upper liquid phase can be used, by combination with the formic acid source, for further generation of a stream comprising formic acid and tertiary amine (I). In general, from 10 to 100%, preferably from 50 to 100%, particularly preferably from 80 to 100%, very particularly preferably from 90 to 100% and in particular from 95 to 100%, of the upper liquid phase is recirculated to step (a).

In the context of the present invention, it has surprisingly been found that the upper liquid phase from the phase separation in step (d) is particularly enriched with low-boiling, organic degradation products of the tertiary amine (I), compared to other low-formic acid streams.

For the purposes of the present invention, the term organic decomposition products of the tertiary amine (I) refers to compounds which are formed by chemical transformation of the tertiary amine (I) with parting of bonds originally present, new formation of nitrogen-carbon bonds or chemical transformation of the radicals bound to the nitrogen. Thus, it has been recognized in the context of the invention that tertiary amines (I) tend, for example, to decompose in the presence of formic acid at elevated temperature and elevated pressure, as prevail in individual steps of the process of the invention, to form the corresponding formamide which is N,N-substituted by the radicals of the tertiary amine (I) and the corresponding formate comprising the other radical of the tertiary amine (I). In the case of a tertiary amine (I) having three identical radicals R, for example $C_5$-$C_8$-alkyl, the abovementioned decomposition reaction would, for example, be as follows:

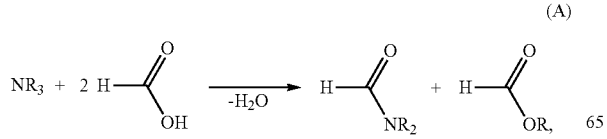

(A)

forming the corresponding dialkylformamide and the corresponding alkyl formate as organic decomposition products of the tertiary amine (I).

Furthermore, it has been recognized in the context of the invention that tertiary amines (I) also tend, for example, to decompose in the presence of formic acid and traces of oxygen at elevated temperature, as can prevail in individual steps of the process of the invention, to form the corresponding formamide which is N,N-substituted by the radicals of the tertiary amine (I) and the aldehyde formed from the other radical. In the case of a tertiary amine (I) having three identical radicals $CH_2$—R, for example $C_5$-$C_8$-alkyl, the abovementioned decomposition reaction would, for example, be as follows:

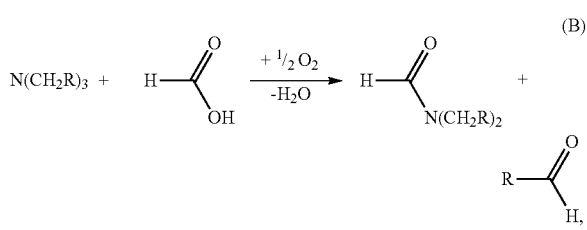

(B)

forming the corresponding dialkylformamide and the corresponding alkanal as organic decomposition products of the tertiary amine (I).

Furthermore, it was recognized in the context of the invention that tertiary amines (I) tend in the presence of methyl formate which is used in obtaining formic acid by hydrolysis of methyl formate to be methylated to the corresponding methyl ammonium cation. In the case of a tertiary amine (I) having three identical radicals R, for example $C_5$-$C_8$-alkyl, the abovementioned methylation reaction would, for example, be as follows, where Me is methyl:

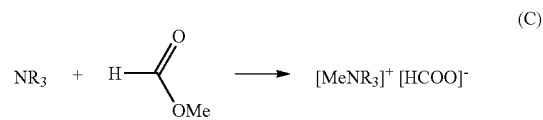

(C)

This can redissociate, also forming a tertiary amine having a methyl group. In the case of the abovementioned system, this reaction equation would be as follows:

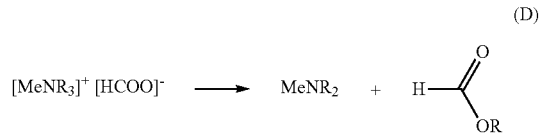

(D)

According to reaction equation (A), the tertiary amine comprising a methyl group then likewise leads to formation of dialkylformamide:

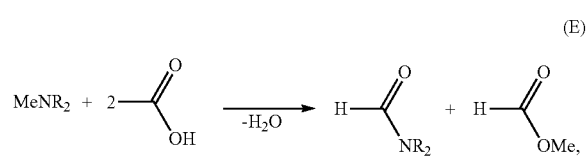

(E)

Organic decomposition products of the tertiary amine (I) can lead to contamination of the formic acid to be obtained as per step (c). In addition, organic decomposition products of the tertiary amine (I) having a boiling point between that of formic acid and the tertiary amine (I) tend to accumulate in the distillation apparatus used in step (c) and thereby increase the energy consumption in the distillation apparatus.

In the context of the invention, it was recognized that any interfering components can be separated off particularly well and in a simple manner by distillation from the abovementioned upper liquid phase from the phase separation in step (d). In the process of the invention, low boilers which at a pressure of 1013 hPa abs have a boiling point which is at least 5° C. lower than that of the tertiary amine (I) are, in step (g), separated off by distillation from the upper liquid phase from the phase separation in step (d) in a distillation apparatus at a temperature at the bottom of from 100 to 300° C. and a pressure of from 1 to 1000 hPa abs and the stream depleted in low boilers is recirculated to one of the abovementioned steps (a) to (f).

Low boilers are generally secondary components as defined in the present description which at a pressure of 1013 hPa abs have a boiling point which is at least 5° C. lower than that of the tertiary amine (I). This preferably has a boiling point which is at least 7° C. lower and particularly preferably at least 10° C. lower than that of the tertiary amine (I). A restriction in terms of a lower limit for the boiling point is not necessary since particularly low-boiling low boilers can generally also be separated off particularly easily by distillation. However, the boiling point of the low boilers at the abovementioned pressure of 1013 hPa abs is generally above 100° C.

The low boilers to be separated off in the process of the invention are either present in the tertiary amine (I) fed to step (a) and/or are formed only during the course of the process up to the present step (g). Thus, it is, for example, possible for the tertiary amine (I) fed to step (a) to comprise various organic decomposition products of the tertiary amine (I) as a result of its production or pretreatment. However, it is also possible and usually also the case that the low boilers to be separated off are formed, either exclusively or in addition to those introduced in the tertiary amine (I), in steps (a) to (c) under appropriate conditions.

The separation in step (g) of the low boilers is carried out by distillation. Possible distillation apparatuses for this purpose are in principle apparatuses which are known to those skilled in the art for such separation tasks or can be designed by a person skilled in the art using general technical knowledge. The distillation apparatus is operated at a temperature at the bottom of from 100 to 300° C. and a pressure of from 1 to 1000 hPa abs. The distillation apparatus is preferably operated at a temperature at the bottom of ≥120° C., particularly preferably ≥140° C., and also preferably ≤220° C. and particularly preferably ≤200° C. The pressure is preferably ≥5 hPa abs, particularly preferably ≥10 hPa abs, and also preferably ≤500 hPa abs and particularly preferably ≤250 hPa abs.

The stream depleted in low boilers is generally obtained as bottom product. However, it is also possible to obtain it as side stream, especially when high boilers possibly present, i.e. generally components having boiling points higher than that of the tertiary amine (I), are to be removed at the same time in the removal of the low boilers by distillation.

In the process of the invention, it is usual to feed from 0.01 to 50% of the upper liquid phase from the phase separation in step (d) to step (g). This amount is sufficient firstly to keep the low boilers present at a sufficiently low level, and secondly to keep the outlay, for example, the size of the distillation apparatus or the ongoing energy consumption, within limits. Preference is given to feeding ≥0.1% and particularly preferably ≥0.5% and also preferably ≤20%, particularly preferably ≤10% and very particularly preferably ≤5%, of the upper liquid phase from the phase separation in step (d) to step (g).

The removal according to the invention of the low boilers in step (g) enables the amount thereof in the process to be kept at a low level. In particular, an accumulation which increases as time goes on is also effectively and cleverly countered in this way.

The concentration of low boilers, based on a stream which comprises the bottom product from step (g) and the remaining upper liquid phase from step (e) which has not been fed to step (g) combined with one another, can easily be kept at a value of ≤25% by weight, preferably ≤15% by weight and particularly preferably ≤10% by weight. In general, the abovementioned concentration is ≥0.001% by weight, usually ≥0.1% by weight. The degree of depletion of low boilers $$\left(1 - \frac{m_{low\ boilers}(\text{depleted stream})[g/h]}{m_{low\ boilers}(\text{feed stream to step }(g))[g/h]}\right) \cdot 100\%$$

is generally from 1 to 100%, preferably ≥10%, particularly preferably ≥50%.

The low boilers which have been separated off can, for example, be disposed of.

The stream depleted in low boilers obtained in step (g) is recirculated to one of the abovementioned steps (a) to (f) in the process of the invention. In general, a total of from 10 to 100%, preferably from 50 to 100%, particularly preferably from 80 to 100%, very particularly preferably from 90 to 100% and in particular from 95 to 100%, of the stream depleted in low boilers is recirculated to steps (a) to (f). It is naturally also possible, for example, to recirculate the stream depleted in low boilers to a selected point, i.e., for example, also to split it and recirculate it to various points. Preference is given to recirculating the stream which has been depleted in low boilers to one of the abovementioned steps (a) to (e). In a particularly preferred embodiment, the stream which has been depleted in low boilers is recirculated to step (a). In another, particularly preferred embodiment, the stream which has been depleted in low boilers is recirculated to step (b).

It is of course also possible in general for further process steps to be integrated into the recirculation of the upper liquid phase from the phase separation from step (d) to step (a), in addition to step (g). The type of intermediate process steps are in principle not subject to any limits. It is also possible to remove part of the upper liquid phase in a targeted manner as "purge stream". Missing amounts of tertiary amine (I) or amounts of this which have been lost can naturally be replaced again by fresh tertiary amine (I) which, for example, can be introduced via the recycle stream or directly into step (a) or at any point in the process, for example in step (b) or step (c).

In the process of the invention, as per step (f), the lower liquid phase from the phase separation is recirculated in step (d) to step (b) and/or (c). This enables the formic acid comprised in the lower liquid phase likewise to be utilized for isolating formic acid by removal by distillation. Depending on the desired embodiment, the lower liquid phase can thus be recirculated (i) to step (b), (ii) partly to step (b) and partly to (c) or (iii) to step (c). However, preference is generally given to recirculation to step (c) since the stressing of the lower liquid phase comprising formic acid and tertiary amine (I) is usually the lowest in this case and the quantity of the stream in step (b) is not increased, which would otherwise have the consequence of correspondingly larger dimensions. In general, from 10 to 100%, preferably from 50 to 100%, particularly preferably from 80 to 100%, very particularly preferably from 90 to 100% and in particular from 80 to 100%, of the lower liquid phase is recirculated to step (b) and/or (c).

However, it is also possible to recirculate a further part of the lower liquid phase to step (a) in addition to the abovementioned recirculation to step (b) and/or (c). This is, for example, advantageous when the formic acid is produced by transition metal-catalyzed hydrogenation of carbon dioxide, since this is generally carried out in the presence of a polar solvent which likewise accumulates in the lower liquid phase and can thus be recirculated to step (a).

It is of course also possible for further process steps to be integrated into the recirculation of the lower liquid phase. As a nonlimiting example, mention may, here too, be made of a purification of the lower liquid phase to be recirculated or of the tertiary amine (I) comprised therein and/or the formic acid comprised therein in order to remove undesirable accompanying materials, reaction by-products or further impurities. The type of intermediate process steps is also in principle not subject to any limits. It is also possible to discharge part of the lower liquid phase in a targeted manner as "purge stream" in order to remove, for example, undesirable accompanying materials, reaction by-products or further impurities.

The tertiary amine (I) which is preferably to be used in the process of the invention has the general formula (Ia)

$$NR^1R^2R^3 \qquad (Ia),$$

where the radicals $R^1$ to $R^3$ are identical or different and are each, independently of one another, an unbranched or branched, acyclic or cyclic, aliphatic, araliphatic or aromatic radical having in each case from 1 to 16 carbon atoms, preferably from 1 to 12 carbon atoms, where individual carbon atoms can also be, independently of one another, replaced by a heterogroup selected from the group consisting of —O— and >N— and two or all three radicals can also be joined to one another to form a chain comprising at least four atoms.

Examples of suitable amines are:

Tri-n-propylamine ($bp_{1013\ hPa}$=156° C.), tri-n-butylamine, tri-n-pentylamine, tri(3-methylbutyl)amine, tri-n-hexylamine, tri-n-heptylamine, tri-n-octylamine, tri-n-nonylamine, tri-n-decylamine, tri-n-undecylamine, tri-n-dodecylamine, tri-n-tridecylamine, tri-n-tetradecylamine, tri-n-pentadecylamine, tri-n-hexadecylamine, tri(2-ethylhexyl)amine, tri(2-propylheptyl)amine.

Dimethyldecylamine, dimethyldodecylamine, dimethyltetradecylamine, ethyl-di(2-propyl)amine ($bp_{1013\ hpa}$=127° C.), di-n-octylmethylamine, di-n-hexylmethylamine, di-n-hexyl(2-methylpropyl)amine, di-n-hexyl(3-methylbutyl)amine, methyl-di(2-ethylhexyl)amine, di-n-hexyl(1-methyl-n-hexyl)amine, di-2-propyldecylamine.

Tricyclopentylamine, tricyclohexylamine, tricycloheptylamine, tricyclooctylamine and derivatives thereof substituted by one or more methyl, ethyl, 1-propyl, 2-propyl, 1-butyl, 2-butyl or 2-methyl-2-propyl groups.

Dimethylcyclohexylamine, methyldicyclohexylamine, diethylcyclohexylamine, ethyldicyclohexylamine, dimethylcyclopentylamine, methyldicyclopentylamine, methyldicyclohexylamine.

Triphenylamine, methyldiphenylamine, ethyldiphenylamine, propyldiphenylamine, butyldiphenylamine, 2-ethylhexyldiphenylamine, dimethylphenylamine, diethyl-phenylamine, dipropylphenylamine, dibutylphenylamine, bis(2-ethylhexyl)phenyl-amine, tribenzylamine, methyldibenzylamine, ethyldibenzylamine and derivatives thereof substituted by one or more methyl, ethyl, 1-propyl, 2-propyl, 1-butyl, 2-butyl or 2-methyl-2-propyl groups.

1,5-Di(1-piperidyl)pentane, N—$C_1$-$C_{12}$-alkylpiperidines, N,N-di-$C_1$-$C_{12}$-alkyl-piperazines, N—$C_1$-$C_{12}$-alkylpyrrolidines, N—$C_1$-$C_{12}$-alkylimidazoles and derivatives thereof substituted by one or more methyl, ethyl, 1-propyl, 2-propyl, 1-butyl, 2-butyl or 2-methyl-2-propyl groups.

1,8-Diazabicyclo[5.4.0]undec-7-ene ("DBU"), 1,4-diazabicyclo[2.2.2]octane, N-methyl-8-azabicyclo[3.2.1]octane ("tropane"), N-methyl-9-azabicyclo[3.3.1]nonane ("granatane"), 1-azabicyclo[2.2.2]octane ("quinuclidine"), 7,15-diazatetracyclo[7.7.1.0$^{2,7}$.0$^{10,15}$]heptadecane ("sparteine").

It is naturally also possible to use mixtures of various tertiary amines (I) in the process of the invention. Naturally, all tertiary amines (I) used then preferably have, at a pressure of 1013 hPa abs, a boiling point which is at least 5° C. higher than that of formic acid.

Among the above-described tertiary amines of the general formula (Ia), preference is in turn given to those in which the radicals $R^1$ to $R^3$ are identical or different and are each, independently of one another, an unbranched or branched, acyclic or cyclic, aliphatic, araliphatic or aromatic radical having in each case from 1 to 16 carbon atoms, preferably from 1 to 12 carbon atoms, where individual carbon atoms may also be, independently of one another, replaced by a heterogroup selected from the group consisting of —O— and >N— and two or all three radicals can also be joined to one another to form a saturated chain comprising at least four atoms.

Preference is given to at least one of the radicals on the alpha-carbon atom, i.e. on the carbon atom bound directly to the amine nitrogen atom, having two hydrogen atoms.

In the process of the invention, particular preference is given to using an amine of the general formula (Ia) in which the radicals $R^1$ to $R^3$ are selected independently from the group consisting of $C_1$-$C_{12}$-alkyl, $C_5$-$C_8$-cycloalkyl, benzyl and phenyl as tertiary amine (I).

Very particular preference is given to using a saturated amine of the general formula (Ia) as tertiary amine (I) in the process of the invention.

In particular, an amine of the general formula (Ia) in which the radicals $R^1$ to $R^3$ are selected independently from the group consisting of $C_5$-$C_8$-alkyl, in particular tri-n-pentylamine, tri-n-hexylamine, tri-n-heptylamine, tri-n-octylamine, dimethylcyclohexyl-amine, methyldicyclohexylamine, dioctylmethylamine and dimethyldecylamine, is used as tertiary amine (I) in the process of the invention.

In a further embodiment, amines which have a branch on the alpha-carbon atom (the carbon atom bound directly to the amine nitrogen atom), on the beta-carbon atom (the second carbon atom from the amine nitrogen atom) or the gamma-carbon atom (the third carbon atom from the amine nitrogen atom) are used. Here, alkyl, aryl and other substituents are conceivable in principle, with preference being given to alkyl groups such as methyl, ethyl or propyl groups or piperidinyl groups. In this embodiment, particular preference is given to N-ethylpiperidine, tri(3-methylbutyl)amine, di-n-hexyl(2-methylpropyl)amine, di-n-hexyl(3-methylbutyl)amine, methyldi(2-ethylhexyl)amine, di-n-hexyl(1-methyl-n-hexyl)amine, di-2-propyldecylamine, methyldicyclohexylamine, 1,5-di(1-piperidyl)pentane.

The streams comprising formic acid and tertiary amine (I) which are formed in the process of the invention can comprise not only free formic acid and the free tertiary amine (I) but also, in admixture with these, formic acid and the tertiary amine (I) in various other forms. The type and amount of the individual forms can differ as a function of the prevailing conditions, for instance the relative ratio of formic acid to tertiary amine (I), the presence of further components (for example water, solvents, by-products, impurities) and thus ultimately also the concentration of formic acid and tertiary amine (I), the temperature and the pressure. Thus, for example, the following conceivable forms may be mentioned:

Ammonium formate (molar ratio of formic acid to tertiary amine (I) of 1) or formic acid-rich adduct with the tertiary amine (I) (molar ratio of formic acid to tertiary amine (I) of >1).

Ionic liquid.

The type and amount of the individual forms is inconsequential for carrying out the process of the invention.

The liquid stream from step (b) to be fed to step (c) can optionally also comprise solvents.

If a solvent is to be used, it is advantageous, particularly in the preferred variant in which two liquid phases are formed in the bottom output from the distillation apparatus mentioned in step (c), for this to be immiscible or only insignificantly miscible with the tertiary amine (I) but readily miscible with the formic acid-comprising amine phase and therefore tending to be present in the lower liquid phase in step (d). A critical parameter here has been found to be an electrostatic factor, also referred to as EF for short, of preferably $\geq 200 \times 10^{-30}$ Cm, at 25° C. The electrostatic factor EF is defined as the product of the relative dielectric constant $\in_r$ and the dipole moment $\mu$ of the solvent (see, for example, C. Reichardt, "Solvents and Solvent Effects in Organic Chemistry", 3rd edition, Wiley-VCH Verlag GmbH & Co KGaA, Weinheim 2003, Chapter 3.2, page 67 bottom to page 68 top). This preferred value ensures that the optional solvent has a certain minimum polarity and is miscible with the lower liquid phase in step (d).

The use of solvents can, depending on the respective system (for example type of tertiary amine (I), concentrations, temperature, pressure and the like) improve, for example, the separation of the two liquid phases.

As classes of substances which are particularly suitable as optional solvent, possibilities are, in particular, formic esters, diols and formic esters thereof, polyols and formic esters thereof, sulfones, sulfoxides, open-chain or cyclic amides and also mixtures of the classes of substances mentioned.

Suitable diols and polyols are, for example, ethylene glycol (EF=$290.3 \times 10^{-30}$ Cm), diethylene glycol (EF=$244.0 \times 10^{-30}$ Cm), triethylene glycol, polyethylene glycol, 1,3-propanediol (EF=$285.6 \times 10^{-30}$ Cm), 2-methyl-1,3-propanediol, 1,4-butanediol (EF=$262.7 \times 10^{-30}$ Cm), dipropylene glycol, 1,5-pentanediol (EF=$212.5 \times 10^{-30}$ Cm), 1,6-hexanediol and glycerol. Due to their OH groups, diols and polyols can be esterified in the presence of formic acid. In the process of the invention, this occurs mainly in step (c) during the thermal separation of the stream comprising formic acid and tertiary amine (I) in the distillation apparatus mentioned. Since the formic esters formed display very similar phase behavior, they are generally likewise well suited as solvents. The water formed in the esterification also does no harm in the thermal separation. An accumulation of water in continuous operation of the process of the invention does not occur since water in these small amounts can be separated off via a side offtake on the distillation apparatus.

Suitable sulfoxides are, for example, dialkyl sulfoxides, preferably $C_1$-$C_6$-dialkyl sulfoxides, in particular dimethyl sulfoxide (EF=$627.1 \times 10^{-30}$ Cm).

Suitable open-chain or cyclic amides are, for example, formamide (EF=$1243.2 \times 10^{-30}$ Cm), N-methylformamide (EF=$2352.9 \times 10^{-30}$ Cm), N,N-dimethyl-formamide (EF=$396.5 \times 10^{-30}$ Cm), N-methylpyrrolidone (EF=$437.9 \times 10^{-30}$ Cm), acetamide and N-methylcaprolactam.

However, it may also be advantageous to use a rather nonpolar solvent having an EF of $<200 \times 10^{-30}$ Cm, at 25° C. Nonpolar solvents may be able to reduce the concentration of formic acid in the upper liquid phase.

However, the process of the invention is preferably carried out without addition of a solvent.

In a preferred variant of the process of the invention, a formic acid source which comprises methyl formate and from which a liquid stream comprising formic acid, tertiary amine (I) and methanol is obtained by hydrolysis of methyl formate is used in the presence of water in step (a). In this variant, the methanol formed from the hydrolysis of methyl formate is then generally also separated off via step (b), in addition to excess water. The methanol which has been separated off can then, for example, be reused in the synthesis of methyl formate. Since methanol has a significantly lower boiling point than water and can thus be separated off relatively easily by distillation from a corresponding mixture comprising methanol, water, formic acid and tertiary amine (I), it is advantageous in this variant to separate off methanol straight away as separate stream from the stream obtained from step (a).

If methanol is separated off in the variant described in the previous paragraph, it is particularly advantageous in step (b) to separate off, likewise straight away, a further stream comprising unreacted methyl formate and to recirculate the latter to step (a). In this way, the yield of formic acid based on the methyl formate used can be increased significantly. Since methyl formate has a significantly lower boiling point than methanol and can thus be separated off even more easily by distillation from a corresponding mixture comprising methyl formate, methanol, water, formic acid and tertiary amine (I), it is advantageous in this variant to separate off methyl formate and methanol straight away as separate streams from the stream obtained from step (a). This can, for example, be carried out in two separate distillation apparatuses in which methyl formate is separated off in the first column and methanol is separated off in the second column. However, it is also possible, for example, to separate off the two components in separate streams in a single distillation apparatus. For example, methyl formate can be obtained as overhead product and methanol can be obtained as side stream product.

The hydrolysis of methyl formate in step (a) usually takes place in a temperature range from 80 to 150° C. and a pressure range from 0.4 to 25 MPa abs. It is in principle possible to use all apparatuses in which an exothermic reaction of fluid streams is possible as apparatus for carrying out the hydrolysis in step (a). Examples which may be mentioned are stirred vessels, tube reactors or shell-and-tube reactors, in each case without internals or with internals (for example beds, packing elements, perforated plates and the like). The hydrolysis is preferably carried out with removal of heat or adibatically.

In another preferred variant of the process of the invention, a formic acid source which comprises carbon dioxide, hydrogen and a homogeneous catalyst and from which a liquid stream comprising formic acid and tertiary amine (I) is obtained by homogeneously catalyzed hydrogenation of carbon dioxide is used in step (a). If step (a) was additionally carried out in the presence of water and/or methanol, which is a particularly preferred embodiment of this variant, then in general, in step (b), water and/or methanol are separated off again, where, in the case of the removal of methanol, this is preferably recirculated back to step (a). In this variant, methanol and water serve first and foremost as polar solvents.

The specific steps and process features of the homogeneously catalyzed hydrogenation of carbon dioxide to formic acid in the presence of water and methanol are described in PCT/EP 2011/060012.

As homogeneous catalyst, preference is given to using a metal-organic complex comprising an element of group 8, 9 or 10 of the Periodic Table. The complex preferably further comprises at least one phosphine group having at least one unbranched or branched, acyclic or cyclic aliphatic radical having from 1 to 12 carbon atoms, where individual carbon atoms can also be replaced by >P—. The hydrogenation is preferably carried out at from 20 to 200° C. and from 0.2 to 30 MPa abs. The output from the hydrogenation stage (a) is preferably a two-phase mixture. The upper phase comprises tertiary amine (I) and homogeneous catalyst, while the lower phase comprises formic acid, tertiary amine (I), water, methanol and likewise homogeneous catalyst. The two phases are separated and the upper phase comprising tertiary amine (I) and homogeneous catalyst is recirculated to the hydrogenation stage (a). The lower phase comprising formic acid, tertiary amine (I), water, methanol and homogeneous catalyst is preferably extracted with tertiary amine (I) in order to extract the major part of the homogeneous catalyst present therein and recirculate it together with the tertiary amine (I) likewise to the hydrogenation stage (a). The remainder of the lower phase, which comprises formic acid, tertiary amine (I), water and methanol, is then recirculated to step (b) in order then to separate off, as described above, methanol and according to the invention water and organic decomposition products of the tertiary amine (I).

As regards the further work-up, mention may also be made, for the purpose of supplementary information, of the specific steps and process features mentioned in PCT/EP 2011/060012.

FIG. 1 shows a simplified block diagram of a general embodiment of the process of the invention. In the figure, the individual letters have the following meanings:
    A=apparatus for producing a stream comprising formic acid and tertiary amine (I)
    B=apparatus for separating off secondary components
    C=distillation apparatus
    D=phase separation vessel
    F=distillation apparatus A formic acid source is fed via stream (1) and tertiary amine (I) is fed via stream (8c) to the apparatus A for producing a stream comprising formic acid and tertiary amine (I). As indicated above, the formic acid source to be fed in can comprise, for example, formic acid in chemically bound form or a precursor by means of which formic acid is produced by chemical reaction in apparatus A. The stream (2) comprising formic acid and tertiary amine (I) is taken off from apparatus A and fed to apparatus B for the removal of secondary components. This apparatus can be, for example, a distillation apparatus in which low-boiling secondary components are removed by distillation. Secondary components which have been separated off are taken off via stream (3). The stream concentrated in formic acid and tertiary amine (I) is fed via stream (4) to the distillation apparatus C. Here, formic acid is separated off by distillation as stream (5). The bottoms from the distillation apparatus C are fed as stream (6) to the phase separation vessel D for phase separation. The lower liquid phase is recirculated as stream (7) to the distillation apparatus C. The upper liquid phase is taken off as stream (8a) and fed to the distillation apparatus F. In this, low boilers are removed by distillation as stream (8z) and the stream depleted in low boilers is recirculated as stream (8c) to the apparatus A.

Figure 2:
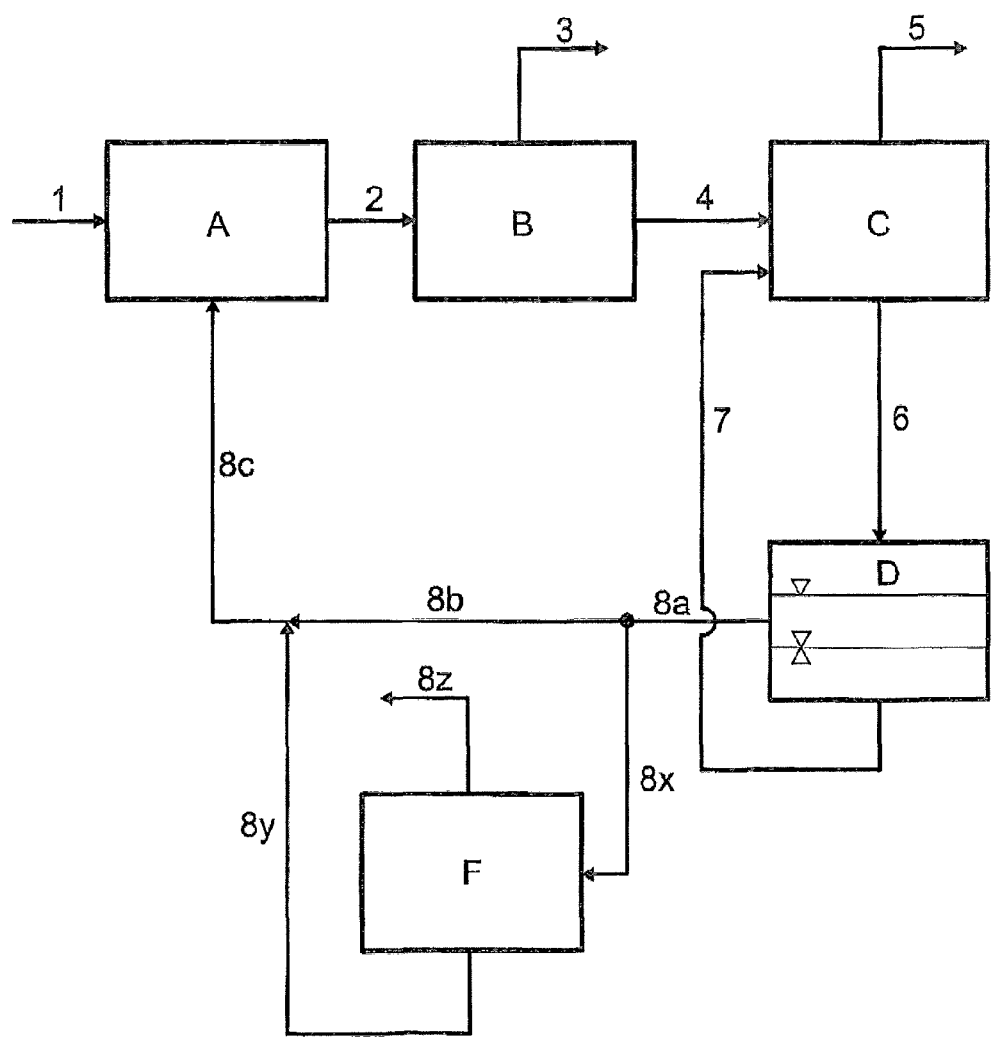
FIG. 2 shows a simplified block diagram of a modified, preferred embodiment in which only part of the upper liquid phase from the phase separation vessel D is fed to the distillation apparatus F for the removal of low boilers.

FIG. 2 shows a simplified block diagram of a modified, preferred embodiment in which only part of the upper liquid phase from the phase separation vessel D is fed to the distillation apparatus F for the removal of low boilers. The other part is recirculated via stream (8b) and subsequently (8c) directly to the apparatus A.

Figure 3:
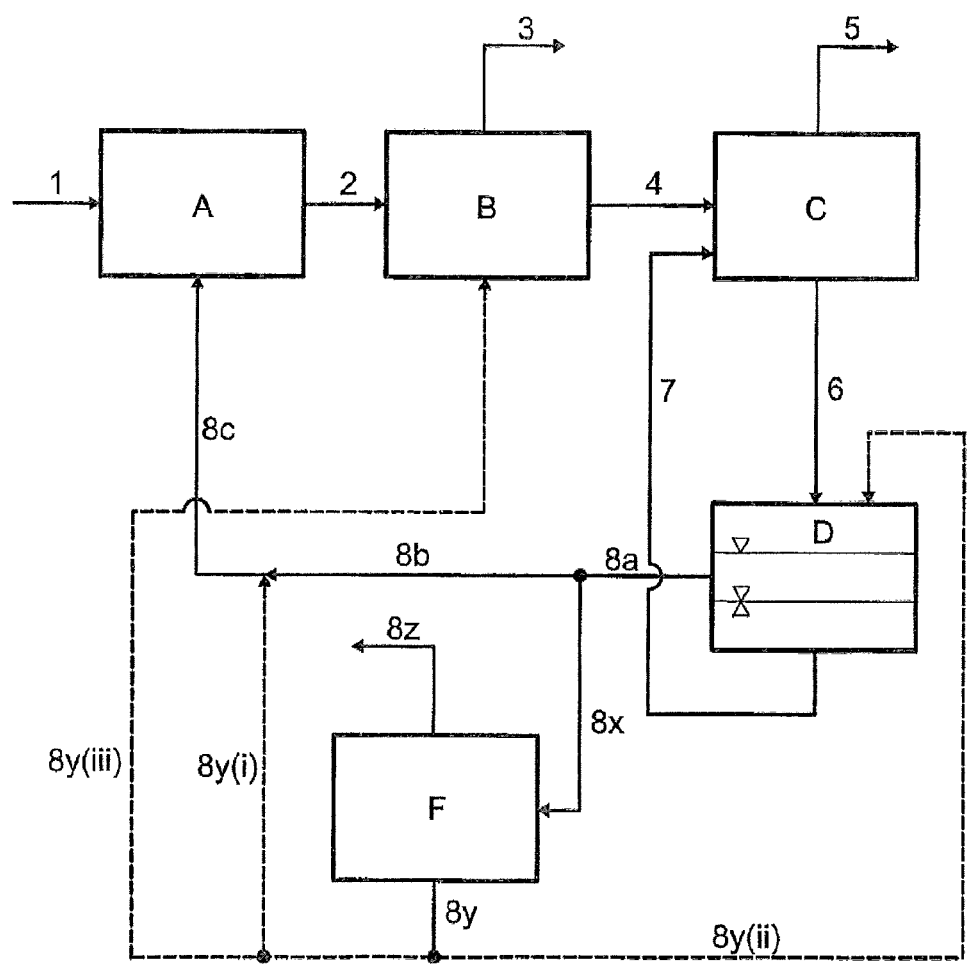
FIG. 3 shows, by means of the streams ($8y(i)$) to ($8y(iii)$) shown as broken lines, illustrative recirculations to apparatus A, to apparatus B and to the phase separation vessel D.

The recirculation of the stream depleted in low boilers from the distillation apparatus F can be carried out to other points in the process. Thus, FIG. 3 shows, by means of the streams (8y(i)) to (8y(iii)) shown as broken lines, illustrative recirculations to apparatus A, to apparatus B and to the phase separation vessel D. The streams shown as broken lines are alternatives which can in each case be present either alone or in combination. However, the recirculation can, for example, also be effected at other points in the process, for example to the distillation apparatus C.

Figure 4:
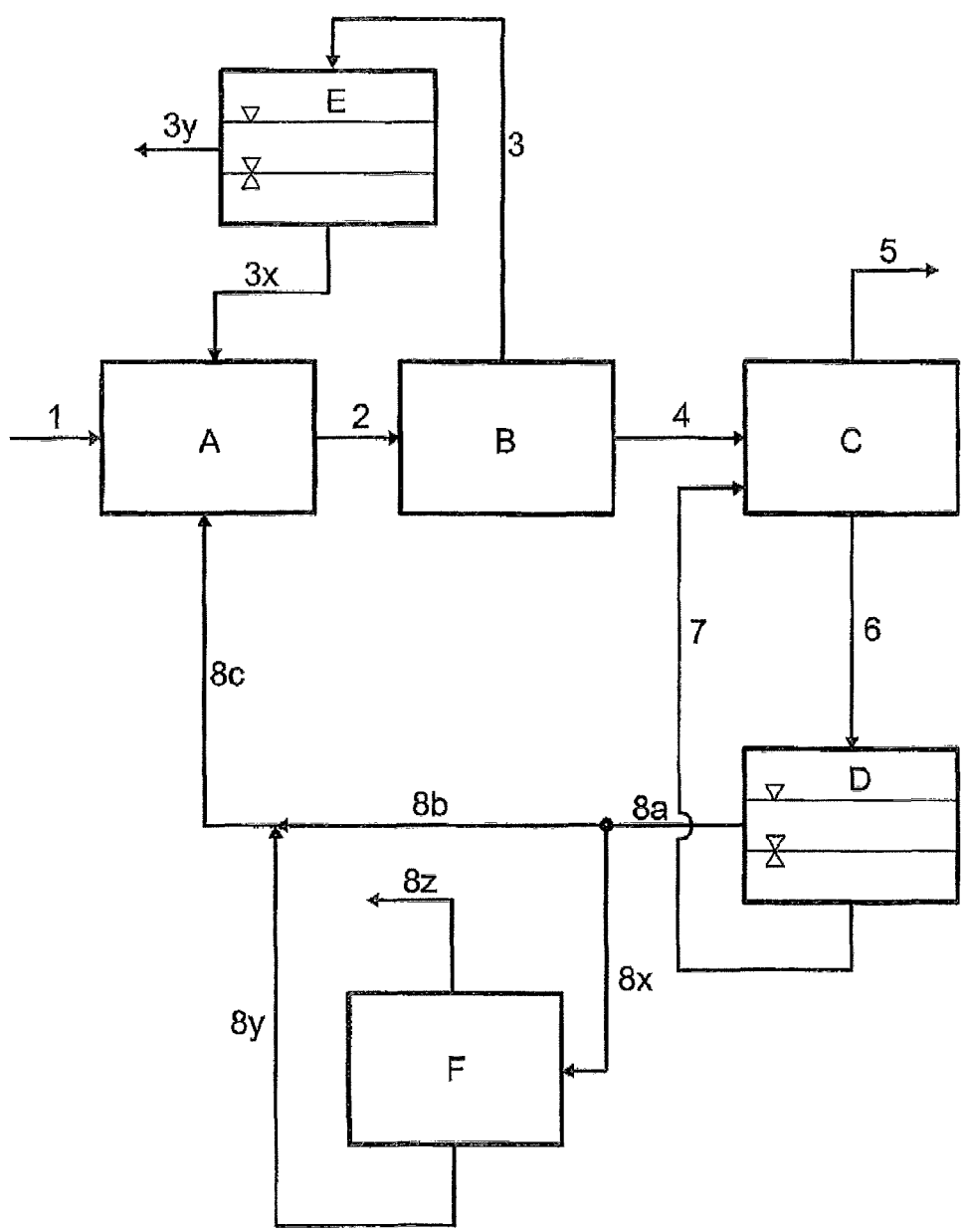
FIG. 4 shows a preferred embodiment in which the removal according to the invention of the low boilers as per the variant shown in FIG. 2 is combined with a particular variant for separating off the secondary components.

FIG. 4 shows a preferred embodiment in which the removal according to the invention of the low boilers as per the variant shown in FIG. 2 is combined with a particular variant for separating off the secondary components. This particular variant is especially advantageous in the presence of water as secondary component and also allows organic decomposition products of the tertiary amine (I) which are formed in the process of the invention to be separated off in one step without being passed on to an appreciable extent to the distillation apparatus C. In FIG. 4, the additional letter E has the following meaning:
    E=phase separation vessel The stream (2) comprising formic acid, tertiary amine (I) and water is taken off from apparatus A and fed to apparatus B in order to separate off water and organic decomposition products of the tertiary amine (I). This apparatus can be, for example, a distillation apparatus. Water and organic decomposition products of the tertiary amine (I) which have been separated off are taken off via stream (3) and fed to the phase separation vessel E. In this, two liquid phases are formed. The lower, water-comprising liquid phase is recirculated as stream (3x) to the apparatus A. The upper liquid phase enriched in organic decomposition products of the tertiary amine (I) is taken off as stream (3y) and discharged from the process. The stream enriched in formic acid and tertiary amine (I) is fed via stream (4) to the distillation apparatus C.

In the region of the distillation apparatus C and the phase separation D, various embodiments are possible. They differ not only in whether the phase separation is carried out in a separate vessel or integrated into the bottom of the distillation column, but also in the location of the introduction of the stream comprising formic acid and tertiary amine (I) into the distillation apparatus and in the flow between the column vessel and the bottom vaporizer and also the place at which the bottom output is taken off. The embodiments shown in FIGS. 2 to 7 of PCT/EP2011/060,770 and described in the text can also be employed for the purposes of the preferred process according to the invention.

Two preferred embodiments for preferred fields of use of the process of the invention are described below.

Preparation of Formic Acid by Hydrolysis of Methyl Formate

Figure 5:
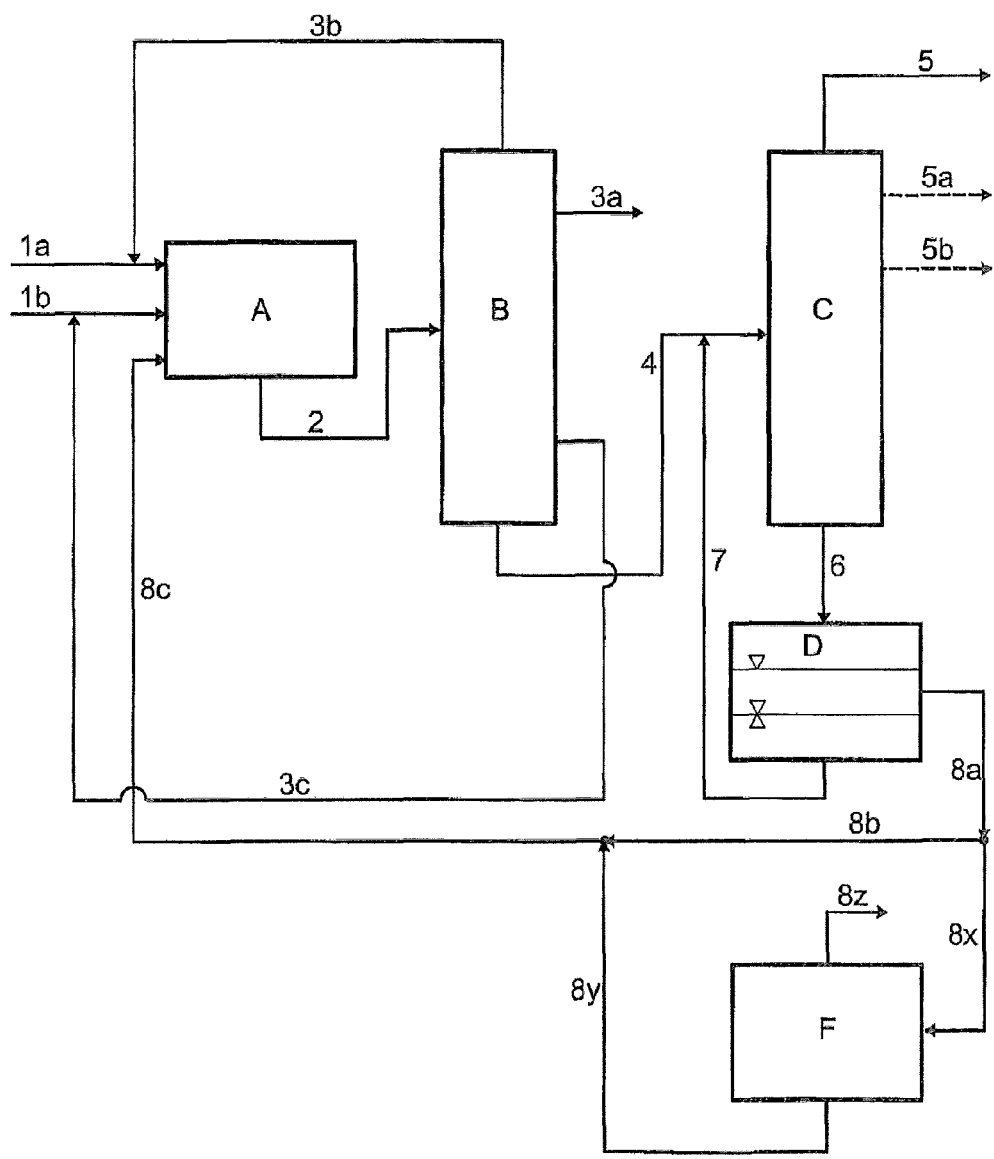
FIG. 5 shows a preferred embodiment for obtaining formic acid by hydrolysis of methyl formate.

A preferred embodiment for obtaining formic acid by hydrolysis of methyl formate is shown in FIG. 5 by means of a simplified block diagram.

In the figure, the individual letters have the following meanings:
    A=apparatus for the hydrolysis of methyl formate and production of a stream comprising formic acid, tertiary amine (I) and water B=distillation apparatus for separating off methyl formate, methanol and water
C=distillation apparatus for obtaining formic acid
D=phase separation vessel
F=distillation apparatus Methyl formate (streams (1a) and (3b)), water (streams (1b) and (3c)) and tertiary amine (I) (stream (8c)) are fed to the apparatus A. A stream comprising formic acid, tertiary amine (I), methanol, water and methyl formate is formed by hydrolysis of methyl formate and is taken off as stream (2) from the apparatus A and fed to the apparatus B. The methyl formate conversion and thus the composition of the stream (2) depends first and foremost on the relative amounts of the three feed streams methyl formate, water and tertiary amine (I) fed to the apparatus A, the type of tertiary amine (I) used, the residence time and the reaction temperature. The conditions appropriate for the respective reaction system can easily be determined by a person skilled in the art, for example by means of preliminary tests. The molar ratio of formic acid to tertiary amine (I) in stream (2) is usually from 0.5 to 5, preferably from 0.5 to 3, with deviations from this range naturally also being possible.

In the distillation apparatus B, unreacted methyl formate (stream (3b)), methanol formed in the hydrolysis (stream (3a)) and water and organic decomposition products of the tertiary amine (I) (stream (3c)) are separated off from stream (2). Stream (3b) comprising the unreacted starting material methyl formate is recirculated to the apparatus A. The methanol separated off via stream (3a) can, for example, be reused for preparing methyl formate. Stream (3c) is likewise recirculated to the apparatus A. Formic acid and tertiary amine (I) are taken off via stream (4). This additionally comprises residual amounts of water. Depending on the way in which the process is carried out, these can amount to a few percent by weight or even some tens of percent by weight of the stream (4). The water content of stream (4) is preferably ≤20% by weight, particularly preferably ≤10% by weight and very particularly preferably ≤5% by weight. The molar ratio of formic acid to tertiary amine (I) is not changed or only insignificantly changed by the distillation apparatus B, so that this ratio is usually also from 0.5 to 5, preferably from 0.5 to 3 in stream (4), with deviations from this range naturally also being possible.

Stream (4) is fed to the distillation apparatus C. In this, the formic acid is removed by distillation via stream (5) as overhead product, via stream (5a) as side product and/or via stream (5b) as side product. Depending on the boundary conditions, i.e. especially the composition of the feed stream (4) to the distillation apparatus C and the desired purity of the formic acid, formic acid can be obtained as stream (5) at the top or as stream (5a) as side product in the present embodiment. Water-comprising formic acid is then taken off as side product via stream (5a) or (5b). In some cases, it may even be sufficient to remove formic acid or water-comprising formic acid purely via stream (5) as overhead product. Depending on the specific embodiment, the side stream (5b) or even both side streams (5a) and (5b) can thus be dispensed with. The distillation apparatus C can naturally also have the embodiments disclosed in FIGS. 2 to 7 of PCT/EP2011/060,770.

The bottom product from the distillation apparatus C is fed as stream (6) to the phase separation vessel D. As an alternative, the phase separator vessel D can also be integrated into the distillation apparatus C. The bottom product is separated into two liquid phases in the phase separation vessel D. A heat exchanger, for example, can also optionally be installed between the distillation apparatus C and the phase separation vessel D in order to cool the bottom stream taken off.

Although a lower phase separation temperature generally leads to somewhat better separation in respect of the formic acid content, it results in an additional outlay and energy consumption because of the use of a heat exchanger. Advantages and disadvantages therefore have to be weighed against one another in each case. The lower liquid phase from the phase separation vessel D is recirculated via stream (7) to the distillation apparatus C. The lower liquid phase can also be preheated. This can be effected by means of a heat exchanger which is separate in energy terms or by heat integration with the heat exchanger used for cooling the bottom output from the distillation apparatus C or a combination of the two.

The upper liquid phase from the phase separation vessel D is taken off via stream (8a). A substream (8x) is fed to the distillation apparatus F. In this, low boilers are removed by distillation as stream (8z) and the stream depleted in low boilers is recirculated as stream (8y) and subsequently (8c) to the apparatus A. The remaining, other substream (8b) is recirculated directly via stream (8c) to the apparatus A.

Figure 6:
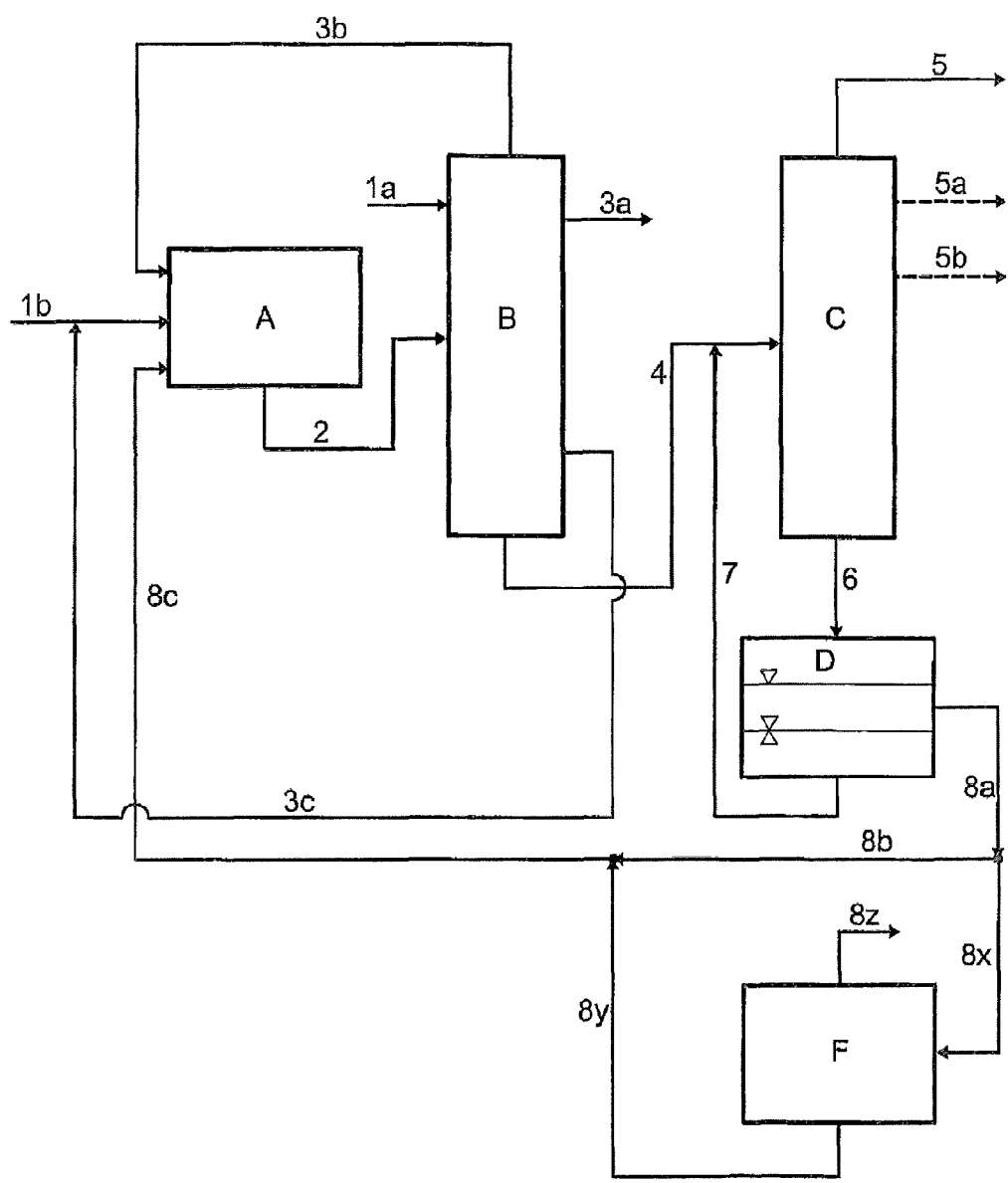
FIG. 6 shows a preferred embodiment for obtaining formic acid by hydrolysis of methyl formate, wherein the methyl formate streams (1a) is introduced into the distillation apparatus B.

In another, preferred embodiment for obtaining formic acid by hydrolysis of methyl formate, the methyl formate stream (1a) is introduced into the distillation apparatus B as shown in FIG. 6. This embodiment is generally advantageous when the methyl formate available as stream (1a) is still contaminated with residual amounts of methanol, for example due to a preceding methyl formate synthesis stage with partial conversion of methanol and incomplete work-up of the methyl formate. As a result of the direct introduction of stream (1a) into the distillation apparatus B, the methanol comprised can be separated off as stream (3a) and, for example, recirculated to the methyl formate synthesis stage. This variant makes it possible to omit a methyl formate/methanol separation entirely in the methyl formate synthesis stage and thus to save an entire distillation column and thus also energy in ongoing operation.

Figure 7:
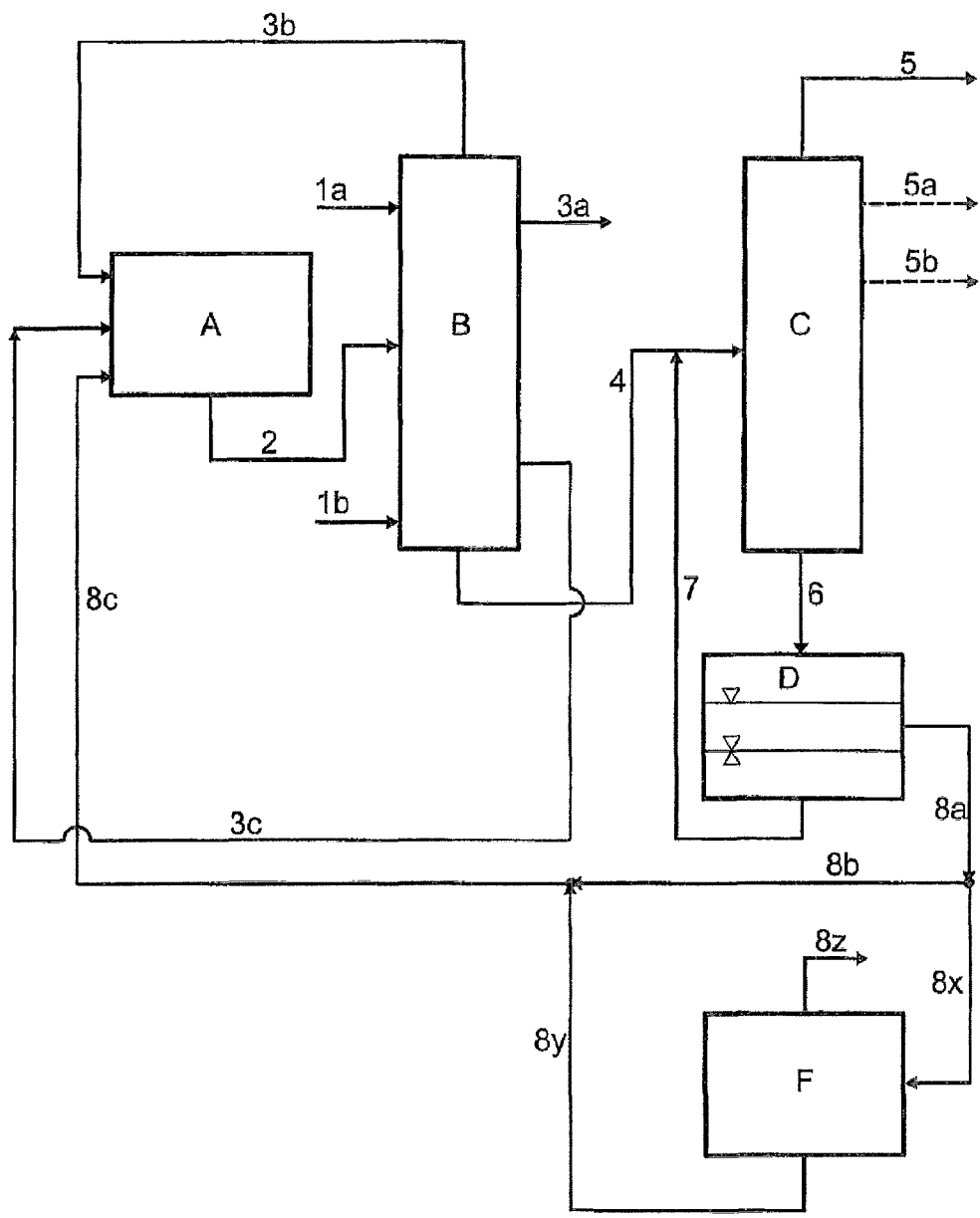
FIG. 7 shows a preferred embodiment for obtaining formic acid by hydrolysis of methyl formate, wherein both the methyl formate stream (1a) and the water stream (1b) are introduced into the distillation apparatus B.

In a further, preferred embodiment for obtaining formic acid by hydrolysis of methyl formate, both the methyl formate stream (1a) and the water stream (1b) are introduced into the distillation apparatus B as shown in FIG. 7. As regards the water stream (1b), this embodiment is generally advantageous when hot condensate or steam is available as water source, since in this way the thermal energy stored therein can be utilized in the distillation apparatus B.

For the sake of completeness, it may be mentioned that, in a further embodiment, it is naturally also possible to introduce the methyl formate stream (1a) into the apparatus A but the water stream (1b) into the distillation apparatus B. This is advantageous when, for example, low-pressure excess steam is available.

Figure 8:
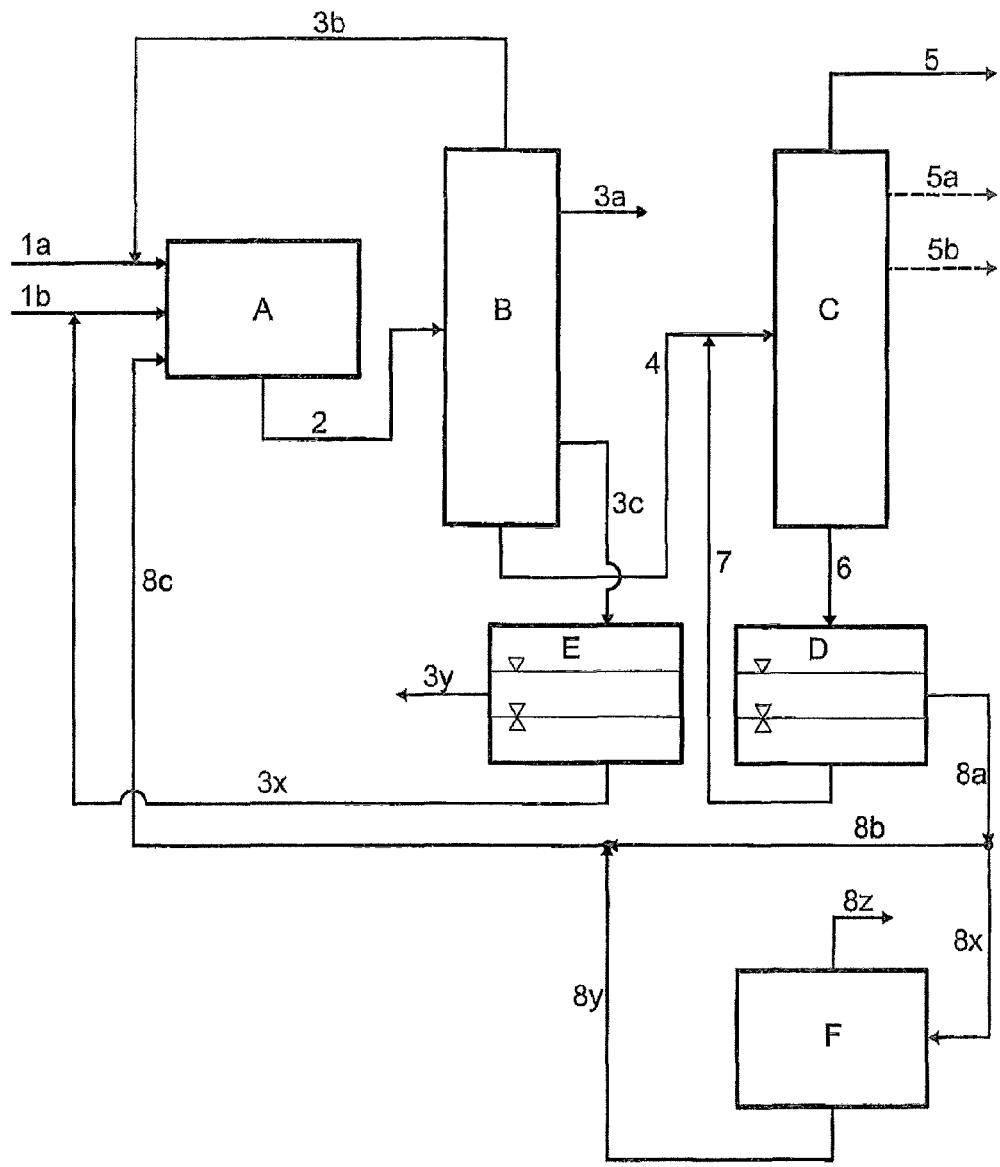
FIG. 8 shows a combination of the variants from FIGS. 4 and 5.

In the preparation of formic acid by hydrolysis of methyl formate, too, it is naturally also possible and even advantageous to combine the variants shown in FIGS. 5 to 7 with the specific removal of secondary components shown in FIG. 4. This is shown by way of example as a combination of the variants from FIGS. 4 and 5 in FIG. 8.

Figure 9:
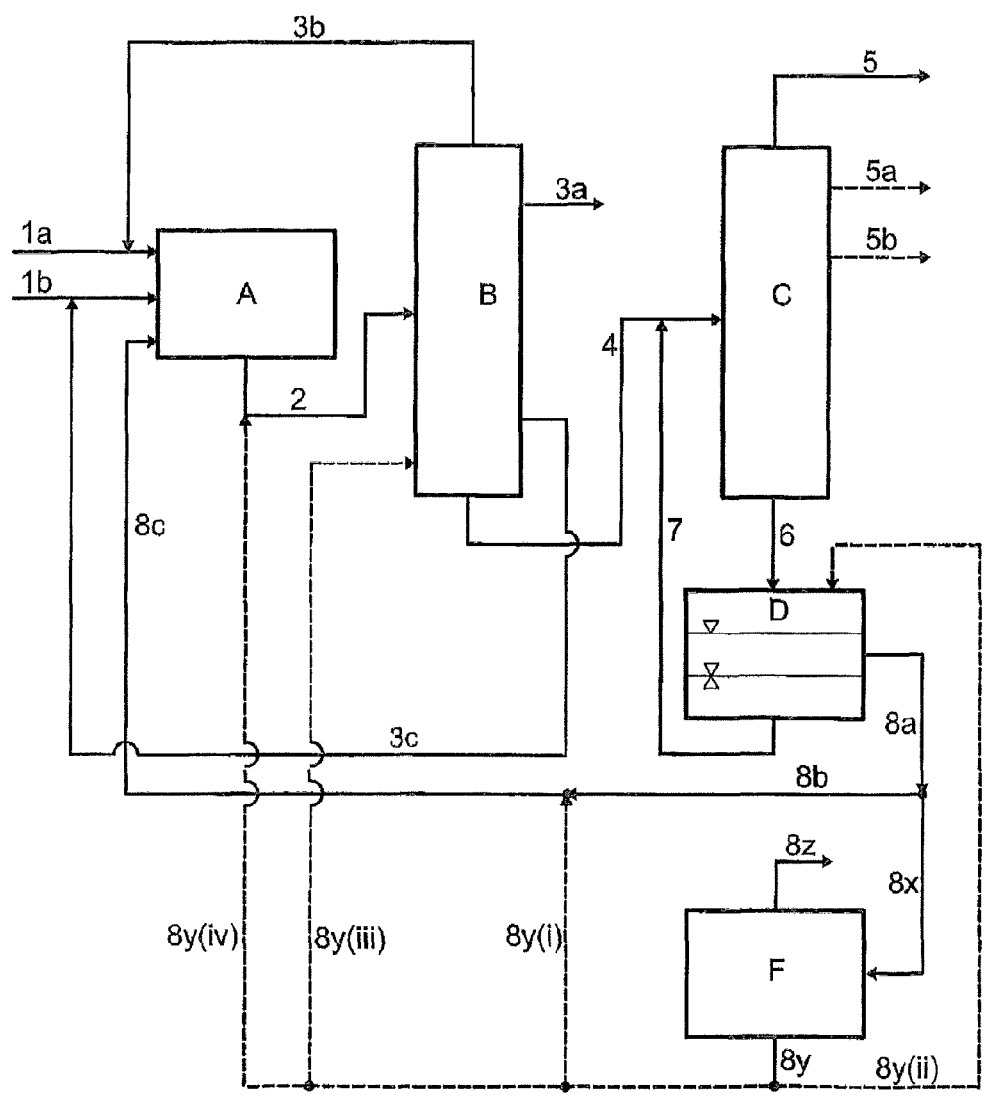
FIG. 9 shows, by means of the streams (8y(i)) to (8y(iv)) shown as broken lines, illustrative recirculations to apparatus A, to apparatus B (two different positions of introduction) and to the phase separation vessel D.

It is likewise possible, in the variants shown in FIGS. 5 to 8, in a manner similar to that mentioned above in connection with FIG. 3, to recirculate the stream depleted in low boilers from the distillation apparatus F not only to the apparatus A but also or exclusively to other points in the process. Thus, FIG. 9 shows, by means of the streams (8y(i)) to (8y(iv)) shown as broken lines, illustrative recirculations to apparatus A, to apparatus B (two different positions of introduction) and to the phase separation vessel D. The streams shown as broken lines are alternatives which can in each case be present individually or in combination. Of course, recirculations not shown, e.g. to the distillation apparatus C are likewise conceivable.

Figure 10:
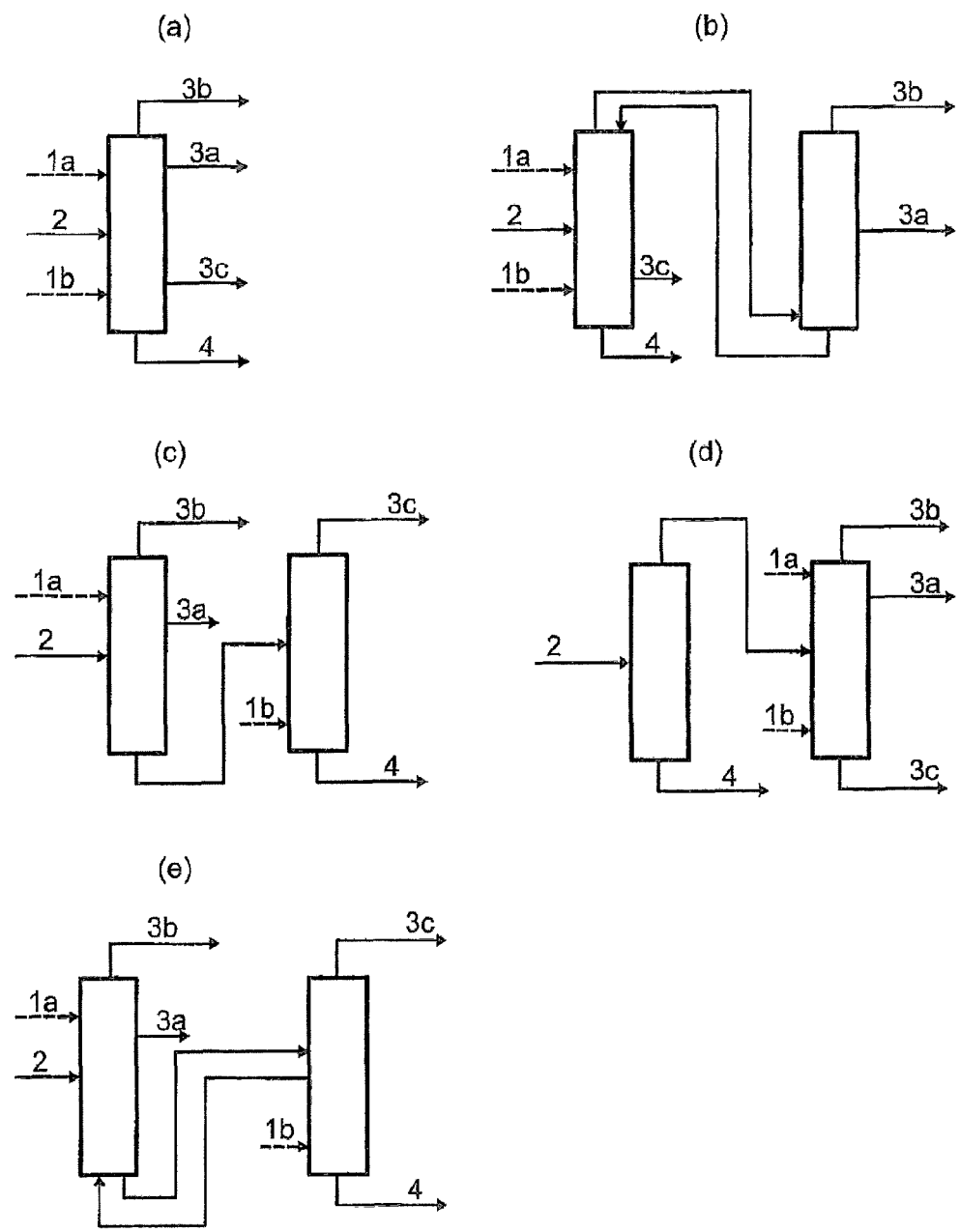
FIG. 10 shows embodiments of the distillation apparatus B having one or two distillation columns.
Figure 11:
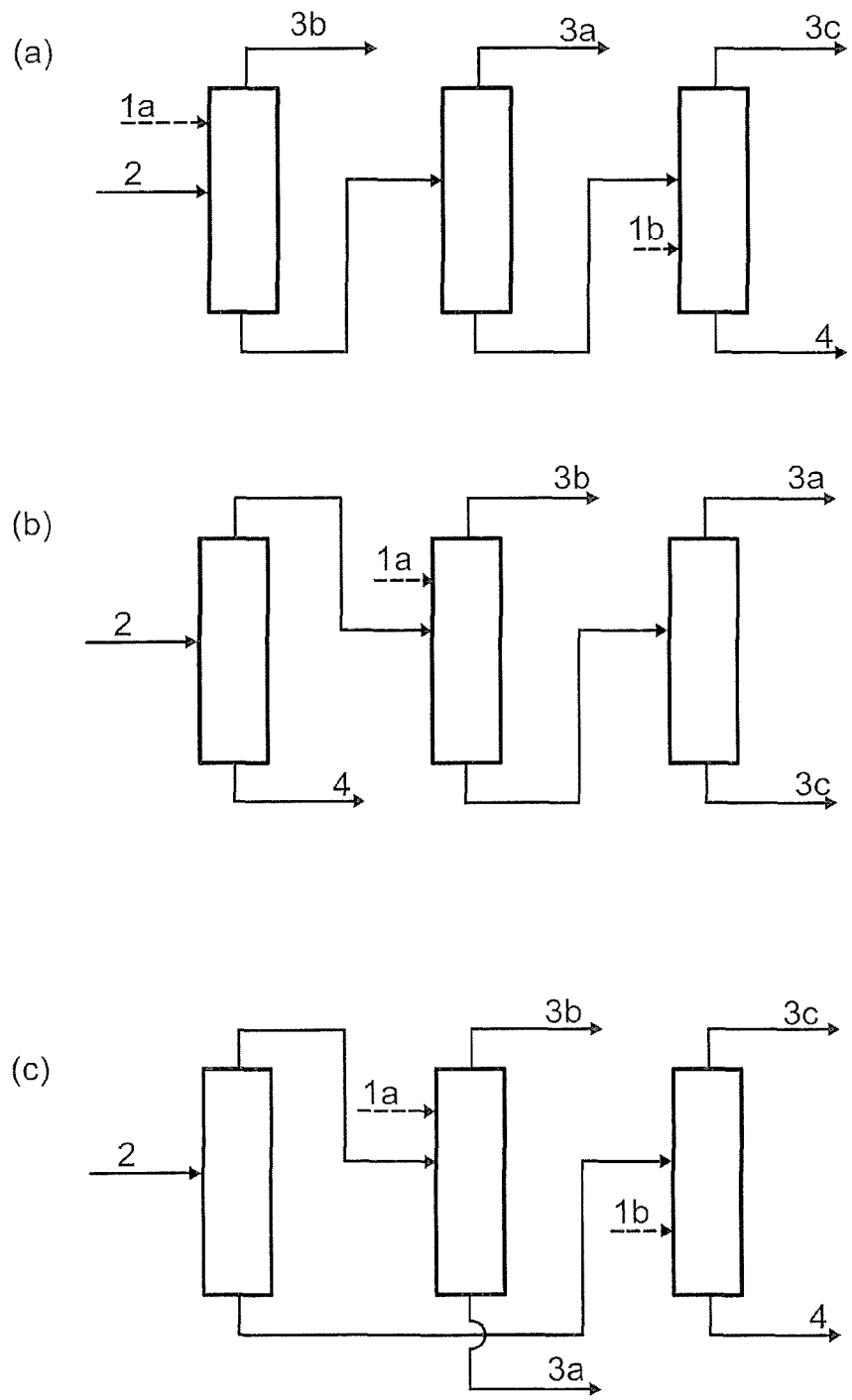
FIG. 11 shows embodiments of the distillation apparatus B having three distillation columns.

In the variants of FIGS. 5 to 9, specific variants in respect of the embodiment of the distillation apparatus B having one, two or even three distillation columns are possible. FIG. 10a shows an embodiment having one distillation column. FIGS. 10b to 10e show different embodiments having two distillation columns. FIG. 11a to 11c show different embodiments having three distillation columns. The variants having one or two distillation columns are preferred for the design of the distillation apparatus B. For the sake of completeness, it may be mentioned that, particularly in the embodiments having one or two distillation columns, these can also be configured as thermally coupled columns or a dividing wall column.

Preparation of Formic Acid by Hydrogenation of Carbon Dioxide

Figure 12:
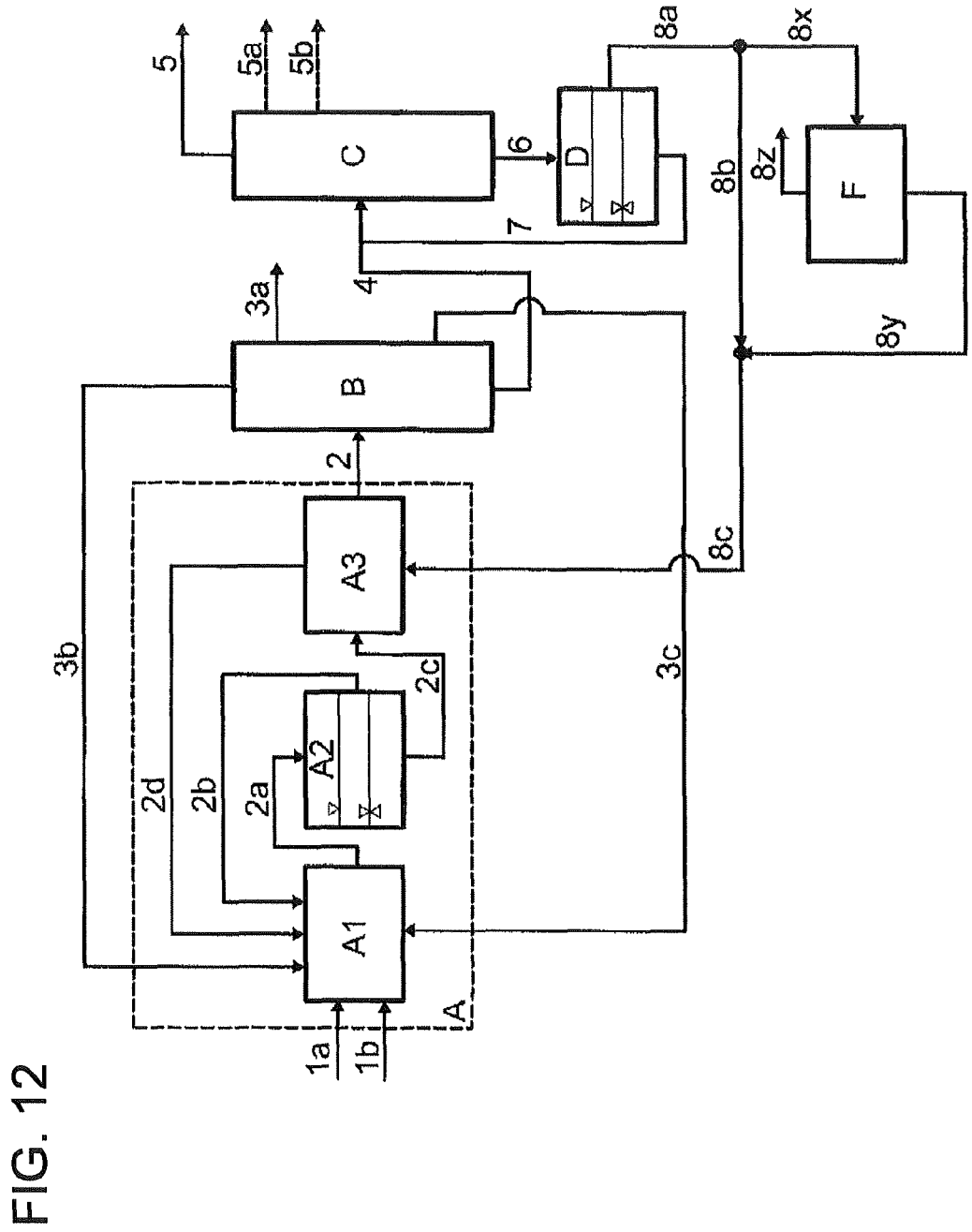
FIG. 12 shows a preferred embodiment for obtaining formic acid by hydrogenation of carbon dioxide.

A preferred embodiment for obtaining formic acid by hydrogenation of carbon dioxide is shown in FIG. 12 by means of a simplified block diagram.

In the figure, the individual letters have the following meanings:
A=apparatus for the hydrogenation of carbon dioxide and production of a stream comprising formic acid, tertiary amine (I) and water
A1=hydrogenation reactor
A2=phase separation vessel
A3=extraction unit
B=distillation apparatus for separating off methanol, water and organic decomposition products of the tertiary amine (I)
C=distillation apparatus for obtaining formic acid
D=phase separation vessel
F=distillation apparatus Carbon dioxide (stream (1a)), hydrogen (stream (1b)) and tertiary amine (I) (stream (8c)) are fed to the hydrogenation reactor A1 in the apparatus A. In the hydrogenation reactor A1, the hydrogenation proceeds in the presence of a homogeneous catalyst and of water and methanol as solvent to form a stream (2a) comprising formic acid, tertiary amine (I), methanol, water and homogeneous catalyst. This is fed to the phase separation vessel A2 in which two liquid phases are formed. The upper liquid phase comprising tertiary amine (I) and homogeneous catalyst is recirculated via stream (2b) to the hydrogenation reactor A1. The lower liquid phase comprising formic acid, tertiary amine (I), water, methanol and likewise homogeneous catalyst is conveyed via stream (2c) to the extraction unit A3. In this, the residues of the homogeneous catalyst still present are largely extracted by means of the tertiary amine (I) fed in as stream (8) and are recirculated together with the tertiary amine (I) as stream (2d) to the hydrogenation reactor A1. A stream comprising formic acid, tertiary amine (I) and water is thus obtained as stream (2) and fed to the distillation apparatus B.

Methanol (stream (3b)) and water and organic decomposition products of the tertiary amine (I) (stream (3c)) are separated off from stream (2) in the distillation apparatus B. Stream (3b) comprising methanol is recirculated to the hydrogenation reactor A1 in apparatus A. Stream (3c) is likewise recirculated to the hydrogenation reactor A1 in the apparatus A. Formic acid and tertiary amine (I) are taken off via stream (4) and conveyed to the distillation apparatus C. With regard to the process steps in respect of the distillation apparatus C, the phase separation vessel D and the distillation apparatus F, reference may be made to the above description of the preparation of formic acid by hydrolysis of methyl formate.

Naturally, in the preparation of formic acid by hydrogenation of carbon dioxide, it is also possible, in a manner similar to that mentioned above in connection with FIG. 3, to recirculate the stream depleted in low boilers from the distillation apparatus F not only to the apparatus A but also or exclusively to other points in the process.

The process of the invention makes it possible to obtain formic acid in high yield and high concentration by thermal separation of a stream comprising formic acid and a tertiary amine.

The removal according to the invention of low boilers from the upper liquid phase from the phase separation of the bottom output from the thermal separation of the stream comprising formic acid and tertiary amine enables the concentration of the low boilers in the system to be kept at a low level. In this way, the gradual accumulation of low boilers is avoided and a slow increase in the energy consumption in the distillation apparatus for the thermal separation of the stream comprising formic acid and tertiary amine and also a slow deterioration in the formic acid quality as a result of increasing contamination with low boilers are thus effectively countered. The process of the invention can thus be operated very stably with, at the same time, constant high purity of the formic acid produced over long operating times. The formic acid obtained has a low color number and a high color number stability. The process can be carried out simply, reliably and with a low energy consumption.

The process of the invention can, in particular, also be used particularly advantageously in conjunction with the hydrolysis of methyl formate as formic acid source and has technical and economic advantages over the production process of methyl formate hydrolysis with subsequent dewatering by means of an extractant or a two-pressure distillation which is at present performed in the industry.

Examples

Laboratory Plant 1 (for Comparative Example 1)

Figure 13:
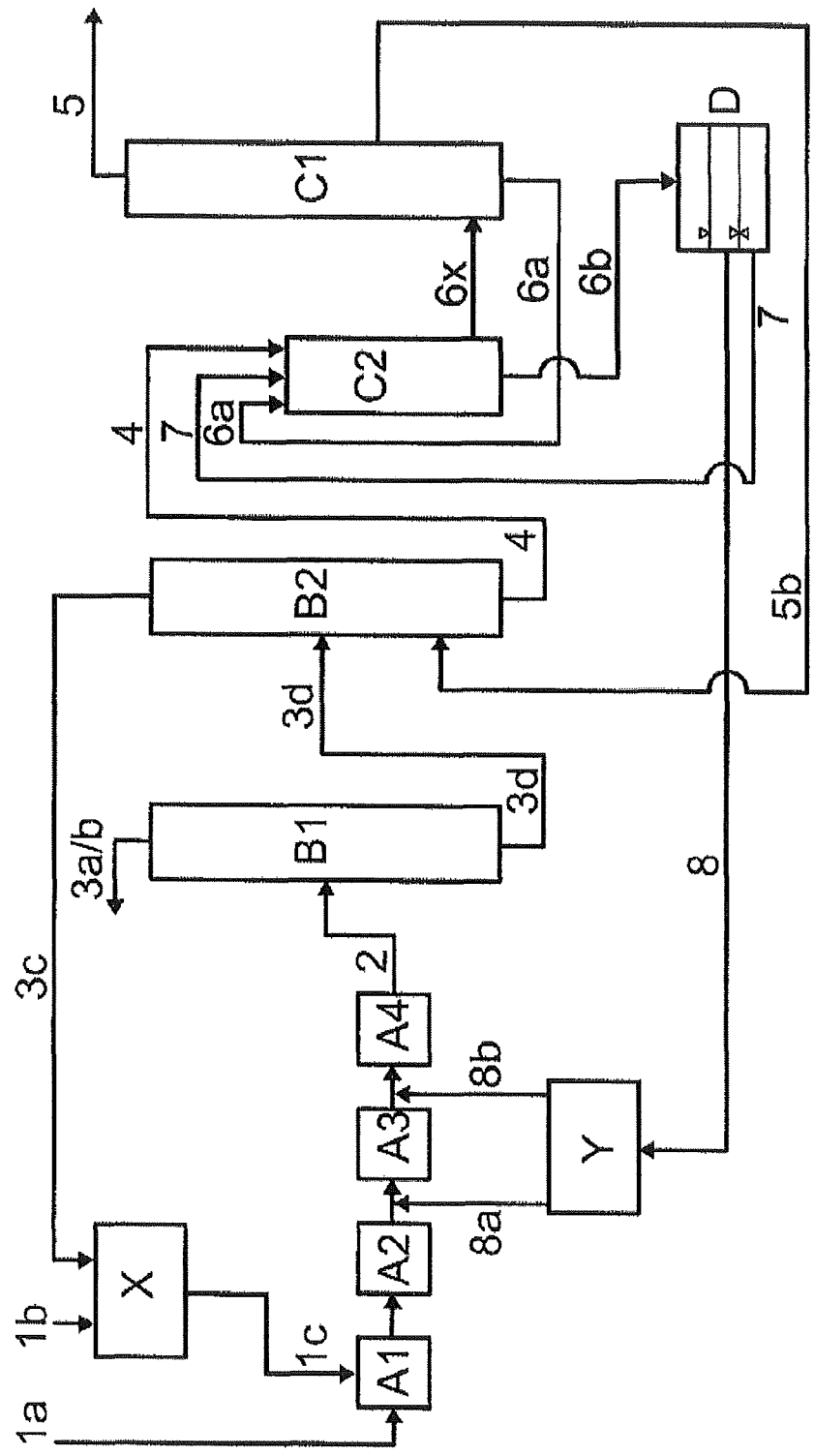
FIG. 13 shows the simplified block diagram of laboratory plant 1.

Laboratory plant 1 was employed for examining the continuous process without use of the present invention. The simplified block diagram of laboratory plant 1 is shown in FIG. 13. In the figure, the individual letters have the following meaning:
A1=stirred vessel (volume 0.3 l, electrically heated)
A2, 3, 4=in each case (internal diameter 80 mm, length 1200 mm, filled with 2 mm glass spheres, electrically heated)
X=Mixing vessel (volume 5 l)
Y=Vessel (volume 5 l)
B1=Distillation apparatus comprising column body (internal diameter 55 mm, equipped with two mesh packings each having a packing height of 1.3 m and a specific surface area of 750 m$^2$/m$^3$, with the inlet for stream (2) being located between the two mesh packings), oil-heated falling film evaporator and condenser and also regulable runback distributor at the top of the column
B2=Distillation apparatus comprising column body (internal diameter 55 mm, equipped with 12 bubble cap trays in the stripping section and 10 bubble cap trays in the enrichment section, with the inlet for stream (3d) being located between the two sections and the inlet for stream (5b) being located in the stripping section), oil-heated falling film evaporator and condenser and alsoregulable runback distributor at the top of the column
C1=column body (internal diameter 43 mm, equipped with a mesh packing above the bottom having a packing height of 0.66 m and a specific surface area of 500 m²/m³ and also a further mesh packing having a packing height of 1.82 m and a specific surface area of 750 m²/m³, with the side offtake for stream (5b) being located between the two mesh packings) and condenser and also regulable runback distributor at the top of the column C2=oil-heated falling film evaporator D=separate phase separation vessel (volume 0.3 l, oil-heated)

The apparatus and lines are composed of a nickel-based alloy having the material number 2.4610. The mass flows were measured by means of a coriolis flow meter. Laboratory plant 1 was operated continuously.

In all experiments in the laboratory plant 1, the content of formic acid was in each case determined by potentiometric titration with 0.5 N NaOH in water and the content of water was determined by the Karl Fischer method. All other organic components were in each case determined by gas chromatography.

Laboratory Plant 2 (for Example 2 According to the Invention)

Figure 14:
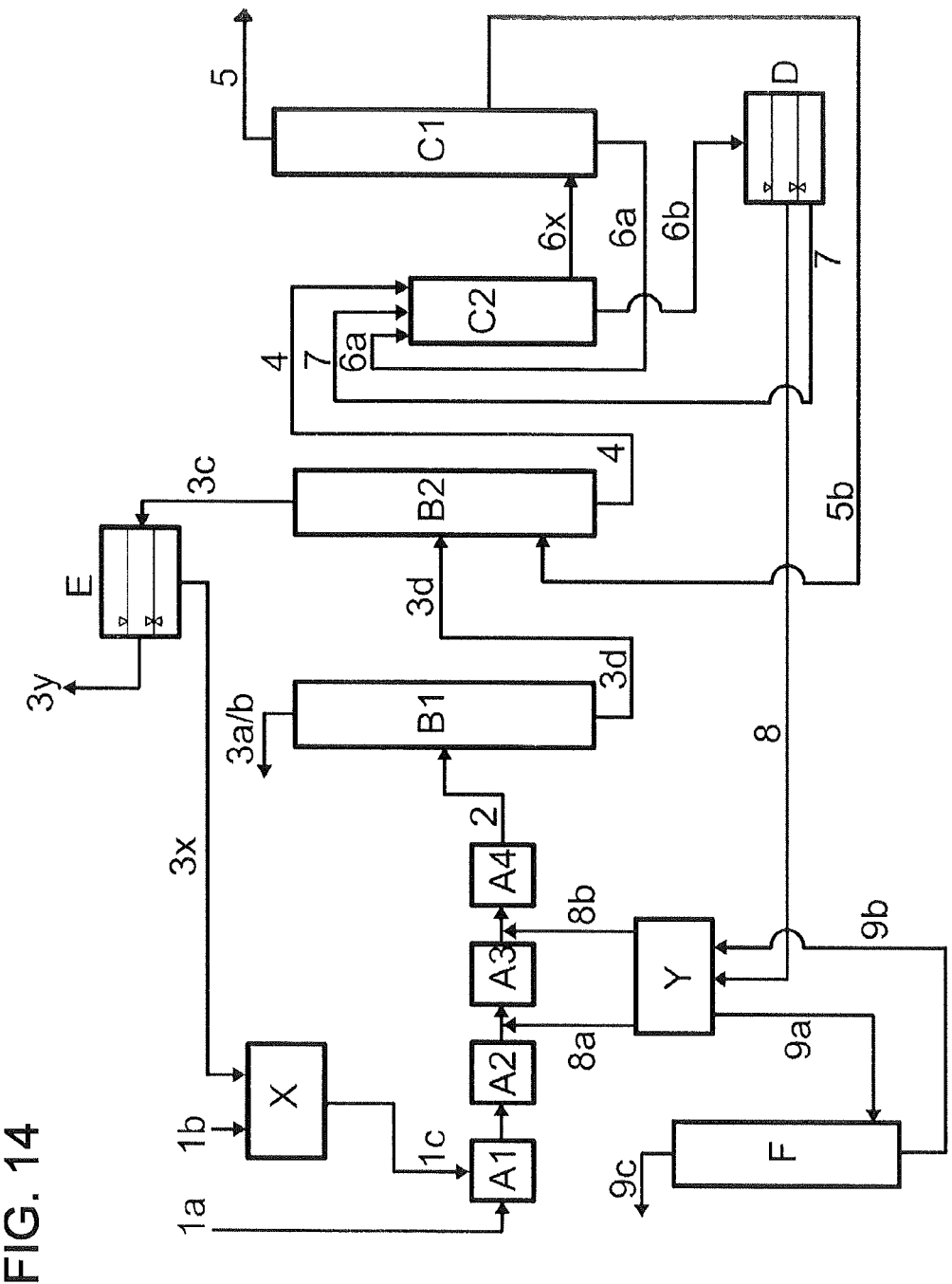
FIG. 14 shows the simplified block diagram of laboratory plant 2.

Laboratory plant 2 is laboratory plant 1 expanded by a separate phase separation vessel for stream (3c) and was employed for examining the continuous process using the present invention. The simplified block diagram of laboratory plant 2 is shown in FIG. 14. In the figure, the additional letters have the following meanings:

E=Phase separation vessel

F=Distillation apparatus comprising column body (internal diameter 30 mm, equipped with 1 m of Sulzer CY packing (750 m²/m³), with the inlet for stream (9a) being located below the packing), oil-heated bottom vessel and also regulable runback distributor at the top of the column otherwise, reference is made to the description of laboratory plant 1.

Example 1

Comparative Example

Example 1 was carried out in laboratory plant 1. By means of metering pumps, 1760 g/h of methyl formate as stream (1a) and 849 g/h of water as stream (1c) were metered into the stirred vessel A1. Stream (1c) was taken off from the mixing vessel X and was composed of fresh water via stream (1b) and recycle water from the distillation apparatus B2 via stream (3c). Stream (1b) was selected so that the sum of stream (1b) and stream (3c) gave the desired stream (1c). The stirred vessel A1 was operated at 110° C. and 1.3 MPa abs. The output was introduced into tube reactor A2 which was likewise operated at 110° C. and 1.3 MPa abs. The output from tube reactor A2 was introduced into tube reactor A3. 1964 g/h of tri-n-hexylamine were fed via stream (8a) into the latter. The output from tube reactor A3 was introduced into tube reactor A4. A further 1661 g/h of tri-n-hexylamine were fed via stream (8b) into the latter. Streams (8a) and (8b) were taken off from the vessel Y which served to distribute tri-n-hexylamine recirculated via stream (8) over the two tube reactors A3 and A4. Tube reactor A3 was operated at 115° C. and 1.3 MPa abs, and tube reactor A4 was operated at 110° C. and 1.3 MPa abs. A product mixture comprising 58.4% by weight of tri-n-hexylamine, 16.4% by weight of formic acid, 12.3% by weight of methanol, 7.8% by weight of water and 6.9% by weight of methyl formate was obtained as stream (2).

Stream (2) was depressurized and introduced into the column body of the distillation apparatus B1. At a pressure at the top of 0.18 MPa abs and a reflux ratio of 2.5, a mixture comprising methanol formed and unreacted methyl formate was taken off as overhead product stream (3ab). As bottom product, 5012 g/h of a mixture comprising 71.2% by weight of tri-n-hexylamine, 9.1% by weight of water, 20.7% by weight of formic acid and 0.1% by weight of methanol was obtained as stream (3d). The temperature at the bottom of B1 was 117° C.

Stream (3d) was introduced into the column body of the distillation apparatus B2. In addition, 277 g/h of the side offtake stream from the column body of the distillation apparatus C1, comprising 79.3% by weight of formic acid and 16.6% by weight of water, were fed in via stream (5b). As overhead product from the distillation apparatus B2, 450 g/h of stream (3c) were taken off at a pressure at the top of 0.10 MPa abs and a reflux ratio of 0.71. Stream (3c) which comprised 98.8% by weight of water and 0.3% by weight of formic acid, was fed to the mixing vessel X for recirculation to the stirred vessel A1.

As bottom product, 4821 g/h of a mixture comprising 75.3% by weight of tri-n-hexylamine, 26.0% by weight of formic acid and 1.2% by weight of water were obtained as stream (4) at a temperature at the bottom of B2 of 160° C. and were fed to the top of the evaporator C2. The evaporator C2 and the column body C1 were operated under reduced pressure. The temperature at the lower outlet from the evaporator C2 was 161° C. The gaseous output from the evaporator was fed as stream (6x) to the column body C1. The latter was operated at a pressure at the top of 0.015 MPa abs and a reflux ratio of runback to distillate of 4. As overhead product from C1 907 g/h of 99.6% by weight strength formic acid were obtained as stream (5). As side offtake stream, 277 g/h were taken off as stream (5b) and recirculated to the column body B2. The liquid output from the column body C1 was fed as stream (6a) to the top of the evaporator C2.

The liquid output from the evaporator C2 was introduced as stream (6b) into the phase separation vessel D. This was operated at atmospheric pressure and a temperature of 80° C. Two liquid phases were formed. The upper liquid phase was continuously taken off at 3587 g/h as stream (8) and conveyed to the vessel Y. Stream (8) comprised 95.7% by weight of tri-n-hexylamine and 1.2% by weight of formic acid. The lower liquid phase was conveyed continuously as stream (7) to the evaporator C2. The remaining stream was fed into the top of the evaporator C2.

Figure 15:
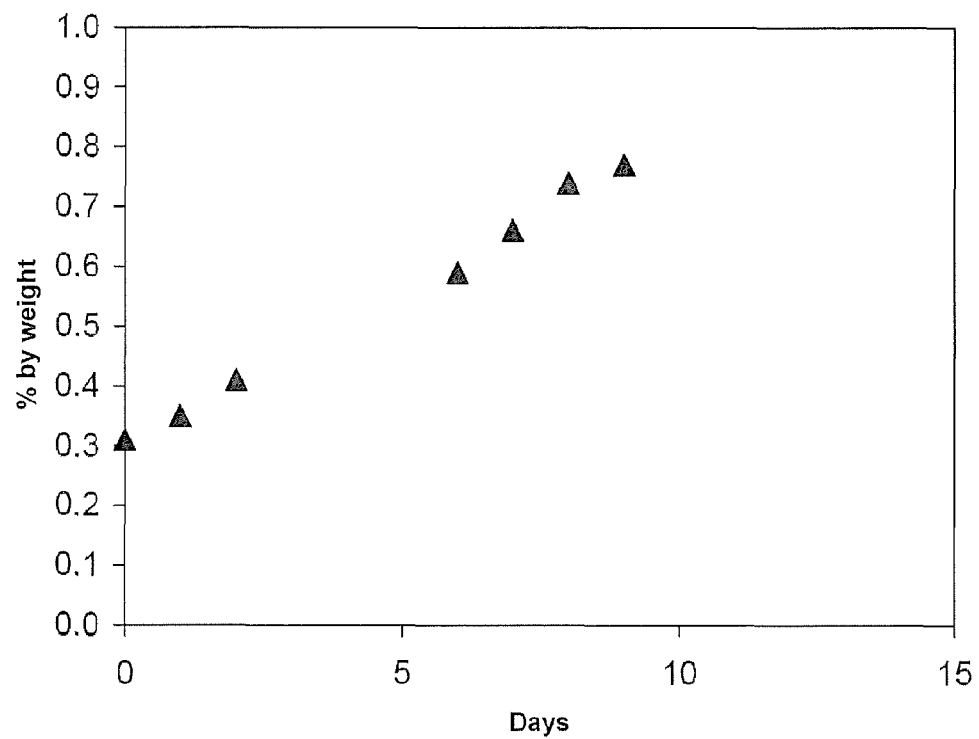
FIG. 15 shows the methyldi-n-hexylamine concentration of Example 1 in graphical form.

To ensure the abovementioned operating state, the plant was firstly run-in for seven days. During this time, the methyldi-n-hexylamine concentration in stream (8) rose to 0.31% by weight and continued to rise steadily in the following days. 9 days after start-up, the concentration was 0.77% by weight. An end to the rise could not be discerned. The methyldi-n-hexylamine concentration is shown in tabular form in table 1 and in graphical form in FIG. 15.

Example 1 shows that without the use of the measure according to the invention for the targeted isolation and discharge of low boilers, in the present example especially methyldi-n-hexylamine, the concentration of these in stream (8) increases continuously. Example 1 also demonstrates that methyldi-n-hexylamine is also formed under real operating conditions. Disadvantages in the long-term operation of such a process would be preprogrammed.

Example 2

Example According to the Invention

Example 2 was carried out in laboratory plant 2. By means of metering pumps, 2280 g/h of methyl formate as stream (1a)

and 950 g/h of water as stream (1c) were metered into the stirred vessel A1. Stream (1c) was taken off from the mixing vessel X and was composed of fresh water via stream (1b) and recycle water from the distillation apparatus B2 via stream (3c). Stream (1b) was selected so that the sum of stream (1b) and stream (3c) gave the desired stream (1c). The stirred vessel A1 was operated at 110° C. and 1.3 MPa abs. The output was introduced into tube reactor A2 which was operated at 108° C. and 1.3 MPa abs. The output from tube reactor A2 was introduced into tube reactor A3. 1603 g/h of tri-n-hexylamine were fed via stream (8a) into the latter. The output from tube reactor A3 was introduced into tube reactor A4. A further 1603 g/h of tri-n-hexylamine were fed via stream (8b) into the latter. Streams (8a) and (8b) were taken off from the vessel Y which served to distribute tri-n-hexylamine recirculated via stream (8) over the two tube reactors A3 and A4. Tube reactor A3 was operated at 105° C. and 1.3 MPa abs, and tube reactor A4 was operated at 106° C. and 1.3 MPa abs. A product mixture comprising 49.8% by weight of tri-n-hexylamine, 16.9% by weight of formic acid, 12.3% by weight of methanol, 7.9% by weight of water and 11.5% by weight of methyl formate was obtained as stream (2).

Stream (2) was depressurized and introduced into the column body of the distillation apparatus B1. At a pressure at the top of 0.18 MPa abs and a reflux ratio of 1.4, a mixture comprising methanol formed and unreacted methyl formate was taken off as overhead product stream (3ab). As bottom product, 5007 g/h of a mixture comprising 59.5% by weight of tri-n-hexylamine, 9.9% by weight of water, 26.3% by weight of formic acid and 0.1% by weight of methanol was obtained as stream (3d). The temperature at the bottom of B1 was 117° C.

Stream (3d) was introduced into the column body of the distillation apparatus B2. In addition, 265 g/h of the side offtake stream from the column body of the distillation apparatus C1, comprising 83.2% by weight of formic acid and 16.6% by weight of water, were fed in via stream (5b). As overhead product from the distillation apparatus B2, 600 g/h of stream (3c) were taken off at a pressure at the top of 0.18 MPa abs and a reflux ratio of 0.25. Stream (3c) which comprised 97.9% by weight of water and 2.0% by weight of formic acid, was fed to the mixing vessel X for recirculation to the stirred vessel A1.

As bottom product, 4512 g/h of a mixture comprising 63.9% by weight of tri-n-hexylamine, 27.9% by weight of formic acid and 1.0% by weight of water were obtained as stream (4) at a temperature at the bottom of B2 of 177° C. and were fed to the top of the evaporator C2. The evaporator C2 and the column body C1 were operated under reduced pressure. The temperature at the lower outlet from the evaporator C2 was 161° C. The gaseous output from the evaporator was fed as stream (6x) to the column body C1. The latter was operated at a pressure at the top of 0.015 MPa abs and a reflux ratio of runback to distillate of 2.6. As overhead product from C1 930 g/h of 99.6% by weight strength formic acid were obtained as stream (5). As side offtake stream, 265 g/h were taken off as stream (5b) and recirculated to the column body B2. The liquid output from the column body C1 was fed as stream (6a) to the top of the evaporator C2.

The liquid output from the evaporator C2 was introduced as stream (6b) into the phase separation vessel D. This was operated at atmospheric pressure and a temperature of 80° C. Two liquid phases were formed. The upper liquid phase was continuously taken off at 3250 g/h as stream (8) and conveyed to the vessel Y. Stream (8) comprised 95.1% by weight of tri-n-hexylamine and 1.2% by weight of formic acid. The lower liquid phase was taken off continuously as stream (7) and fed into the top of the evaporator C2.

Every weekday (Monday to Friday), 790 g were taken off from vessel Y and distilled in the distillation apparatus F at a pressure at the top of 15 hPa abs and a temperature at the bottom of 162° C. Each time, about 35 g of overhead product were obtained and discarded. The overhead product in each case comprised about 67.1% by weight of methyldi-n-hexylamine, about 0.2% by weight of tri-n-hexylamine and about 28.5% by weight of formic acid. The bottom output remaining in each case was fed back to the vessel Y. At weekends (Saturday and Sunday) no work-up by distillation using the distillation apparatus F was carried out.

Figure 16:
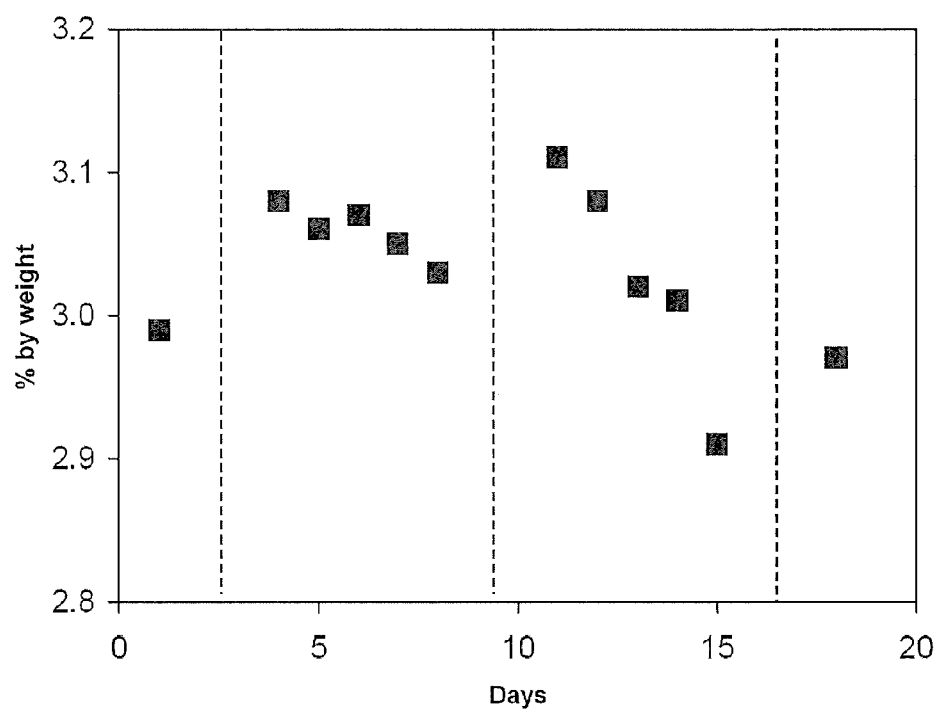
FIG. 16 shows the methyldi-n-hexylamine concentration of Example 2 in graphical form.

The methyldi-n-hexylamine concentration in stream (8) was monitored analytically during the experiment. It is shown in tabular form in table 2 and in graphical form in FIG. 16. The broken, vertical lines in FIG. 16 in each case symbolize the weekend (Saturday and Sunday) during which no work-up by distillation in the distillation apparatus F was carried out.

Example 2 shows that without the use of the measure according to the invention for the targeted isolation and discharge of low boilers, in the present example especially methyldi-n-hexylamine, the concentration of these increases continually. Thus, for example, a rise in stream (8) from 2.99% by weight to 3.08% by weight of methyldi-n-hexylamine was found on the first weekend of the measurements. On the other hand, the concentration of methyldi-n-hexylamine could be reduced again by means of the measure according to the invention during the following five weekdays (Monday to Friday).

The ultimate result is therefore that the concentration of methyldi-n-hexylamine could be kept to a value of about 3% by weight under the process conditions indicated.

Examples 3 to 4

Decomposition of Tri-n-Hexylamine in Comparison with Methyldi-n-Hexylamine

Example 3

Decomposition of Tri-n-Hexylamine in the Presence of Formic Acid and Water 95.3 g (0.35 mol) of tri-n-hexylamine, 16.3 g (0.35 mol) of formic acid (98-100% by weight) and 6.3 g (0.35 mol) of water were mixed in an ice bath in the laboratory. The solution obtained was subsequently warmed to room temperature (about 20° C.) and degassed by evacuation (2 hPa abs) and admission of pure nitrogen, carried out a total of three times. A two-phase solution was obtained. This was then transferred under an $N_2$ atmosphere in a glove box into a 270 ml autoclave (material: HC) and the autoclave was closed. The autoclave was subsequently pressurized with nitrogen to 1.0 MPa abs and heated to 160° C. while stirring vigorously. After the temperature had been reached, a total pressure of 2.5 MPa abs was set by injection of further $N_2$. The reaction mixture was then stirred at 160° C. for 72 hours. The autoclave was subsequently cooled to room temperature, depressurized to atmospheric pressure and the contents were transferred to a glass vessel. The output separated into two phases. 48.1 g of upper phase and 57.9 g of lower phase were obtained. Both phases were analyzed by gas chromatography to determine their di-n-hexylformamide content. The upper phase comprised 0.16% by weight (0.077 g) of di-n-hexylformamide, and the lower phase comprised 0.69% by weight (0.4 g) of di-n-hexylformamide.

Example 4

Decomposition of Methyldi-n-Hexylamine in the Presence of Formic Acid and Water 69.8 g (0.35 mol) of methyldi-n-hexylamine, 16.3 g (0.35 mol) of formic acid (98-100% by weight) and 6.3 g (0.35 mol) of water were mixed in an ice bath in the laboratory. The solution obtained was subsequently warmed to room temperature (about 20° C.) and degassed by evacuation (2 hPa abs) and admission of pure nitrogen, carried out a total of three times. A two-phase solution was obtained. This was then transferred under an $N_2$ atmosphere in a glove box into a 270 ml autoclave (material: HC) and the autoclave was closed. The autoclave was subsequently pressurized with nitrogen to 1.0 MPa abs and heated to 160° C. while stirring vigorously. After the temperature had been reached, a total pressure of 2.5 MPa abs was set by injection of further $N_2$. The reaction mixture was then stirred at 160° C. for 72 hours. The autoclave was subsequently cooled to room temperature, depressurized to atmospheric pressure and the contents were transferred to a glass vessel. The output separated into two phases. 25.0 g of upper phase and 54.3 g of lower phase were obtained. Both phases were analyzed by gas chromatography to determine their di-n-hexylformamide content. The upper phase comprised 0.52% by weight (0.13 g) of di-n-hexylformamide, and the lower phase comprised 1.1% by weight (0.597 g) of di-n-hexylformamide.

Examples 3 and 4 show that the acidolytic formation of di-n-hexylformamide from methyldi-n-hexylamine occurs significantly more quickly than that from tri-n-hexylamine. Since the formation of di-n-hexylformamide equates to a direct loss of tertiary amine (I), it is advantageous in the preparation of formic acid by thermal separation of a stream comprising formic acid and a tertiary amine (I) to keep the amount of methyldi-n-hexylamine as low as possible.

Examples 5 to 7

Influence of Methyldi-n-Hexylamine on the Energy Consumption of the Pure Distillation of Formic Acid Example 5

670 g/h of a mixture from stream (4) from operation of the laboratory plant were fed into a distillation column (internal diameter 30 mm) having 25 bubble trays and an oil-heated Sambay evaporator (thin film evaporator) at an oil temperature of 200° C. and a pressure at the top of 150 hPa abs. The mixture used comprises 20% by weight of formic acid, 74% by weight of tri-n-hexylamine, 2% by weight of water and 1% by weight of di-n-hexylformamide. The reflux ratio at the top of the column was 5:1. Under these conditions, 105 g/h of 99.8% strength formic acid were obtained as overhead product, 10 g/h of 78% strength aqueous formic acid were taken off via a side offtake on the 13$^{th}$ tray and 555 g/h of bottom output were obtained. All streams were combined again in a mixing vessel and fed back to the column. During the experiment, the entire energy input was regulated via the oil temperature in the Sambay evaporator.

Example 6

Example 6 was carried out like example 5 but a mixture derived from stream (4) from the operation of the laboratory plant and enriched with 4% by weight of methyldi-n-hexylamine was fed in. The mixture used comprised 20% by weight of formic acid, 70% by weight of tri-n-hexylamine, 4% by weight of methyldi-n-hexylamine, 2% by weight of water and 1% by weight of di-n-hexylformamide. In contrast to example 5, only 90 g/h of 99.8% strength formic acid were able to be obtained as overhead product when using the methyl di-n-hexylamine-comprising feed stream. The amount of the side offtake stream was 14 g/h, with 80% strength by weight formic acid being obtained here. The remainder was discharged as bottom stream.

Example 7

In example 7, an attempt was made in the apparatus described in example 5 to obtain a similarly large amount of 99.8% strength formic acid as overhead product using the methyldi-n-hexylamine-comprising feed stream mentioned in example 6 by increasing the oil temperature. For this purpose, 666 g/h of the feed stream mentioned in example 6 were fed in. At an oil temperature of 205° C., 103 g/h of 99.8% strength formic acid were able to be obtained as overhead product. 20 g/h of 79% strength by weight formic acid were taken off as side stream. The remainder was discharged as bottom stream.

Examples 5, 6 and 7 demonstrate a significantly adverse effect of the presence of methyldi-n-hexylamine in the pure distillation of formic acid. Under otherwise constant conditions, the amount of pure formic acid which can be achieved decreases significantly. In the present case, only 90 g/h instead of 105 g/h of 99.8% strength formic acid were obtained as overhead product in the presence of 4% by weight of methyldi-n-hexylamine. To compensate for this decrease, an increase in the temperature at the bottom and thus in the energy input is required. In the present case, an increase from 200° C. to 205° C. enabled 103 g/h of 99.8% strength formic acid to be obtained again as overhead product.

Example 8

In the distillation column described in example 5, 650 g/h of the mixture from experiment 7 comprising 20% by weight of formic acid, 2% by weight of water, 4% by weight of methyldi-n-hexylamine and 70% by weight of tri-n-hexylamine were fed in at the bottom at an oil temperature of 194° C. and a pressure at the top of 150 hPa abs. The reflux ratio at the top of the distillation column was 3:1. Under these conditions, an overhead stream of 50 g/h of 99.8% strength formic acid was taken off at the top of the distillation column, a side stream of 75 g/h of 75% strength aqueous formic acid was taken off from the 6$^{th}$ tray of the distillation column and a bottom output of 515 g/h was taken off. The side stream obtained was analyzed to determine its content of tri-n-hexylamine and methyldi-n-hexylamine. It comprises 3000 ppm by weight of tri-n-hexylamine and 35 000 ppm by weight of methyldi-n-hexylamine.

Example 8 shows that a selective increase in the concentration of methyldi-n-hexylamine compared to tri-n-hexylamine by a factor of 10 can be achieved in the side offtake stream of the pure formic acid column.

The invention claimed is:
1. A process for obtaining formic acid by thermal separation of a stream comprising formic acid and a tertiary amine (I) which, at a pressure of 1013 hPa abs, has a boiling point which is at least 5° C. higher than that of formic acid, which comprises

(a) producing a liquid stream comprising formic acid and tertiary amine (I) and having a molar ratio of formic acid to tertiary amine (I) of from 0.5 to 5 by combining tertiary amine (I) and a formic acid source;

(b) separating off from 10 to 100% by weight of secondary components comprised therein from the liquid stream obtained from step (a);

(c) removing formic acid by distillation from the liquid stream comprising formic acid and tertiary amine (I) obtained from step (b) in a distillation apparatus at a temperature at the bottom of from 100 to 300° C. and a pressure of from 30 to 3000 hPa abs, wherein the tertiary amine (I) to be used in step (a) and the degree of separation in the distillation apparatus are selected so that two liquid phases are formed in the bottom output;

(d) separating the bottom output from the distillation apparatus of step (c) into two liquid phases, wherein the upper liquid phase has a molar ratio of formic acid to tertiary amine (I) of from 0 to 0.5 and the lower liquid phase has a molar ratio of formic acid to tertiary amine (I) of from 0.5 to 4;

(e) recirculating the upper liquid phase from the phase separation in step (d) to step (a);

(f) recirculating the lower liquid phase from the phase separation in step (d) to step (b) and/or (c); and (g) separating off low boilers which, at a pressure of 1013 hPa abs, have a boiling point which is at least 5° C. lower than that of the tertiary amine (I) by distillation from the upper liquid phase from the phase separation in step (d) in a distillation apparatus at a temperature at the bottom of from 100 to 300° C. and a pressure of from 1 to 1000 hPa abs, and the stream depleted in low boilers is recirculated to one of the abovementioned steps (a) to (f).

2. The process of claim 1, wherein the formic acid source comprises methyl formate, and a liquid stream comprising formic acid, tertiary amine (I), and methanol is obtained therefrom by hydrolysis of methyl formate in the presence of water in step (a).

3. The process of claim 1, wherein the formic acid source comprises carbon dioxide, hydrogen, and a homogeneous catalyst, and a liquid stream comprising formic acid and tertiary amine (I) is obtained therefrom by homogeneously catalyzed hydrogenation of carbon dioxide.

4. The process of claim 1, wherein the liquid stream produced in step (a) has a concentration of formic acid plus tertiary amine (I) of from 1 to 99% by weight, based on the total amount of the stream.

5. The process of claim 1, wherein the degree of separation in the distillation apparatus of step (c) is selected so that the molar ratio of formic acid to tertiary amine (I) in the bottom output is from 0.1 to 2.0.

6. The process of claim 1, wherein from 0.01 to 50% of the upper liquid phase from the phase separation in step (d) is fed to step (g).

7. The process of claim 1, wherein the stream depleted in low boilers from step (g) is recirculated to step (a).

8. The process of claim 1, wherein the stream depleted in low boilers from step (g) is recirculated to step (b).

9. The process of claim 1, wherein an amine of general formula (Ia), $$NR^1R^2R^3 \qquad (Ia),$$

is used as tertiary amine (I), wherein the radicals $R^1$ to $R^3$ are identical or different and are each, independently of one another, are an unbranched or branched, acyclic or cyclic, aliphatic, araliphatic or aromatic radical having from 1 to 16 carbon atoms, and wherein individual carbon atoms are optionally, independently of one another, replaced by a heterogroup selected from the group consisting of —O— and >N—, and wherein two or all three radicals are optionally joined to one another to form a chain comprising at least four atoms.

10. The process of claim 9, wherein the radicals $R^1$ to $R^3$ are independently selected from the group consisting of $C_1$-$C_{12}$-alkyl, $C_5$-$C_8$-cycloalkyl, benzyl, and phenyl.

11. The process of claim 10, wherein the radicals $R^1$ to $R^3$ are independently $C_5$-$C_8$-alkyl.

* * * * *